US005723747A

United States Patent [19]
Lassner et al.

[11] Patent Number: 5,723,747
[45] Date of Patent: Mar. 3, 1998

[54] WAX ESTERS IN TRANSFORMED PLANTS

[75] Inventors: Michael Lassner; James George Metz, both of Davis, Calif.

[73] Assignee: Calgene, Inc., Davis, Calif.

[21] Appl. No.: 251,464

[22] Filed: Jun. 1, 1994

Related U.S. Application Data

[63] Continuation-in-part of Ser. No. 920,430, Jul. 31, 1992, Pat. No. 5,370,996, which is a continuation-in-part of Ser. No. 796,256, Nov. 20, 1991, abandoned, Ser. No. 767,251, Sep. 27, 1991, Pat. No. 5,403,918, and Ser. No. 659,975, Feb. 22, 1991, abandoned.

[51] Int. Cl.$^6$ .............................. A01H 5/00; A01H 5/10; C12N 15/82
[52] U.S. Cl. ............................ 800/205; 800/DIG. 69; 435/172.3; 435/419; 536/23.6
[58] Field of Search ...................... 800/205, DIG. 69; 435/172.3, 240.4, 320.1, 419; 536/23.6

[56] References Cited

U.S. PATENT DOCUMENTS 4,826,767  5/1989  Hansen.

FOREIGN PATENT DOCUMENTS

| 0 353 872 | 2/1990 | European Pat. Off. . |
| 0 359 472 | 3/1990 | European Pat. Off. . |
| WO92/14816 | 9/1992 | WIPO . |
| WO93/10241 | 5/1993 | WIPO . |

OTHER PUBLICATIONS

Zaka, S. Et al., "Composition of Total Lipids from Acacia–Arabica and Acacia–Farnesiana Seed Oils", *Abstract* vol. 83, (1987) #90499.
Hu, X., et al., "Proportions of C18:1N-7 and C18:1N-9 Fatty Acids in Canola Seedcoat Surface and Internal Lipids", *Journal of the American Oil Chemists Society* (1994) vol. 71, No. 2:221–222.
Trani, M., et al., "Lipase–Catalyzed Production of Wax Esters" *JAOCS*, vol. 68, No. 1 (1991) 20–22.
Hu, X., et al., "Characterization of Wax Sediments in Refined Canola Oils", *JAOCS*, vol. 70, No. 5 (1993) 535–537.
Abstract An 84–014234 *Database WPI Section Ch, Week 8403, Derwent Publications Ltd.*
Weber, N., et al. "Metabolism of Long Chain Alcohols in Cell Suspension Cultures of Soy (Glycine–Max) and Rape (Brassica–Napus) Biological Abstracts" vol. 75, (1983) #75454.
Anderson, et. al. "Characterization of Enzymes Involved in Biosynthesis of Long Chain Liquid Waxes of Jojoba (Simmonosia Chinesis)"; *Plant Physiology* (1992) 99: p. 77.

Fixter, et. al. "Structure, Distribution and Function of Wax Esters in *Acinetobacter calcoaceticus*" *Journal of General Microbiology* (1986) 132 :3147–3157.
Khan, A.A., et al. "Solubilization of Fatty Acid Synthetase, Acyl–CoA Reductase and Fatty Acyl–CoA Alcohol Transacylase from the Microsomes of *Euglena gracilis*" *Archives of Biochemistry and Biophysics* (1975) 178:400–408.
Kolattukudy, P.E., "Cutin, Suberin and Waxes" *The Biochemistry of Plants* (1980) (Stumpf, P.K. and Conn, E.E. Eds.) vol. 4: 571–645.
Kolattukudy, P.E., et. al "Acyl–CoA Reductase and acyl–CoA: Fatty Alcohol acyl Transferase in the Microsomal Preparation from the Bovine Meibomian Gland" *Journal of Lipid Research* (1986) vol. 27:404–411.
Kolattukudy, et al "Enzymatic Reduction of Fatty Acids and a–hydroxy Fatty Acids" *Methods in Enzymology* (1981) vol. 71: 263–275.
Lloyd, Geoffrey M. "Synthesis and Translocation of Lipids in the Cell Envelope Membranes of *Micrococcus cryophilus*; a Comparison of Polar and Neutral Lipids" *Microbios* (1987) 52: 29–37.
Ohlrogge, et. al. "Studies on Biosynthesis of Waxes by Developing Jojoba Seed Tissue" *Lipids* (1978) vol. 13: 203–210.
Pollard, et. al. "Studies on Biosynthesis of Waxes by Developing Jojoba Seed II. The Demonstration of Wax Biosynthesis by Cell–Free Homogenates" *Lipids* (1979) 14 No. 7: 651–662.
Pushnik, et a., "Characterization of the Biosynthetic Pathway for Formtion of Liquid Wax in Jojoba.", Abstract from the Plant Genetic Engineering Laboratory, New Mexico State University, Las Cruces, New Mexico, The Southwest Consortium Fourth Annual Meeting, 7 Feb. 1989.
Wildner, et al. "Wax Ester Biosynthesis in *Euglena Gracilis*" The Southwest Consortium Fifth Annual Meeting, Apr. 22–24, 1990, Las Cruces, N.M.
Wu, et al. "Studies on Biosynthesis of Waxes by Developing Jojoba Seed III. The Demonstration of Wax Esters from Acyl–COA and Long Chain Alcohols" *Lipids* (1981) 16 No. 12 : 897–902.
Pathak et al 1994 Current Science 67 (6) : 470–472.
Cao et al 1987 Pl. Physiol 84: 762–765.

*Primary Examiner*—Elizabeth F. McElwain
*Attorney, Agent, or Firm*—Donna F. Scherer; Carl J. Schwedler

[57] ABSTRACT

The invention provides a method of producing a wax ester in a plant cell whereby a plant cell having a fatty acyl reductase expressed from a sequence heterologous to said plant is grown in the absence of a wax synthase expressed from a sequence which is heterologous to the plant. The invention also provides plant cells containing wax ester.

11 Claims, 6 Drawing Sheets

```
AAATCCTCCA CTCATACACT CCACTTCTCT CTCTCTCTCT CTCTCTCTGA AACAATTGA    60

GTAGCAAACT TAAAAGAAA ATG GAG GAA ATG GGA AGC ATT TTA GAG TTT CTT   112
                     Met Glu Glu Met Gly Ser Ile Leu Glu Phe Leu
                      1               5                       10

GAT AAC AAA GCC ATT TTG GTC ACT GGT GCT ACT GGC TCC TTA GCA AAA    160
Asp Asn Lys Ala Ile Leu Val Thr Gly Ala Thr Gly Ser Leu Ala Lys
             15                  20                  25

ATT TTT GTG GAG AAG GTA CTG AGG AGT CAA CCG AAT GTG AAG AAA CTC    208
Ile Phe Val Glu Lys Val Leu Arg Ser Gln Pro Asn Val Lys Lys Leu
         30                  35                  40

TAT CTT CTT TTG AGA GCA ACC GAT GAC GAG ACA GCT GCT CTA CGC TTG    256
Tyr Leu Leu Leu Arg Ala Thr Asp Asp Glu Thr Ala Ala Leu Arg Leu
     45                  50                  55              60

CAA AAT GAG GTT TTT GGA AAA GAG TTG TTC AAA GTT CTG AAA CAA AAT    304
Gln Asn Glu Val Phe Gly Lys Glu Leu Phe Lys Val Leu Lys Gln Asn
                 65                  70                  75
```

FIGURE 1A

```
TTA GGT GCA AAT TTC TAT TCC TTT GTA TCA GAA AAA GTG ACT GTA GTA       352
Leu Gly Ala Asn Phe Tyr Ser Phe Val Ser Glu Lys Val Thr Val Val
         80                      85                      90

CCC GGT GAT ATT ACT GGT GAA GAC TTG TGT CTC AAA GAC GTC AAT TTG       400
Pro Gly Asp Ile Thr Gly Glu Asp Leu Cys Leu Lys Asp Val Asn Leu
         95                     100                     105

AAG GAA ATG TGG AGG GAA ATC GAT GTT GTC GTT GTC AAT CTA GCT GCT       448
Lys Glu Met Trp Arg Glu Ile Asp Val Val Val Val Asn Leu Ala Ala
        110                     115                     120

ACA ATC AAC TTC ATT GAA AGG TAC GAC GTG TCT CTG CTT ATC AAC ACA       496
Thr Ile Asn Phe Ile Glu Arg Tyr Asp Val Ser Leu Leu Ile Asn Thr
        125                     130                     135         140

TAT GGA GCC AAG TAT GTT TTG GAC TTC GCG AAG AAG TGC AAC AAA TTA       544
Tyr Gly Ala Lys Tyr Val Leu Asp Phe Ala Lys Lys Cys Asn Lys Leu
        145                     150                     155

AAG ATA TTT GTT CAT GTA TCT ACT GCT TAT GTA TCT GGA GAG AAA AAT       592
Lys Ile Phe Val His Val Ser Thr Ala Tyr Val Ser Gly Glu Lys Asn
        160                     165                     170
```

FIGURE 1B

```
GGG TTA ATA CTG GAG AAG CCT TAT ATG GGC GAG TCA CTT AAT GGA        640
Gly Leu Ile Leu Glu Lys Pro Tyr Met Gly Glu Ser Leu Asn Gly
        175                 180                 185

AGA TTA GGT CTG GAC ATT AAT GTA GAG AAG AAA CTT GTG GAG GCA AAA    688
Arg Leu Gly Leu Asp Ile Asn Val Glu Lys Lys Leu Val Glu Ala Lys
        190                 195                 200

ATC AAT GAA CTT CAA GCA GCG GGG GCA ACG GAA AAG TCC ATT AAA TCG    736
Ile Asn Glu Leu Gln Ala Ala Gly Ala Thr Glu Lys Ser Ile Lys Ser
205                 210                 215                 220

ACA ATG AAG GAC ATG GGC ATC GAG AGG GCA AGA CAC TGG GGA TGG CCA    784
Thr Met Lys Asp Met Gly Ile Glu Arg Ala Arg His Trp Gly Trp Pro
            225                 230                 235

AAT GTG TAT GTA TTC ACC AAG GCA TTA GGG GAG ATG CTT TTG ATG CAA    832
Asn Val Tyr Val Phe Thr Lys Ala Leu Gly Glu Met Leu Leu Met Gln
            240                 245                 250

TAC AAA GGG GAC ATT CCG CTT ACT ATT ATT CGT CCC ACC ATC ATC ACC    880
Tyr Lys Gly Asp Ile Pro Leu Thr Ile Ile Arg Pro Thr Ile Ile Thr
255                 260                 265
```

FIGURE 1C

```
AGC ACT TTT AAA GAG CCC TTT CCT GGT TGG GTT GAA GGT GTC AGG ACC    928
Ser Thr Phe Lys Glu Pro Phe Pro Gly Trp Val Glu Gly Val Arg Thr
            270                 275                 280

ATC GAT AAT GTA CCT GTA TAT TAT GGT AAA GGG AGA TTG AGG TGT ATG    976
Ile Asp Asn Val Pro Val Tyr Tyr Gly Lys Gly Arg Leu Arg Cys Met
285                 290                 295                 300

CTT TGC GGA CCC AGC ACA ATA ATT GAC CTG ATA CCG GCA GAT ATG GTC   1024
Leu Cys Gly Pro Ser Thr Ile Ile Asp Leu Ile Pro Ala Asp Met Val
            305                 310                 315

GTG AAT GCA ACG ATA GTA GCC ATG GTG GCG CAC GCA AAC CAA AGA TAC   1072
Val Asn Ala Thr Ile Val Ala Met Val Ala His Ala Asn Gln Arg Tyr
320                 325                 330

GTA GAG CCG GTG ACA TAC CAT GTG GGA TCT TCA GCG GCG AAT CCA ATG   1120
Val Glu Pro Val Thr Tyr His Val Gly Ser Ser Ala Ala Asn Pro Met
            335                 340                 345

AAA CTG AGT GCA TTA CCA GAG ATG GCA CAC CGT TAC TTC ACC AAG AAT   1168
Lys Leu Ser Ala Leu Pro Glu Met Ala His Arg Tyr Phe Thr Lys Asn
350                 355                 360
```

FIGURE 1D

```
CCA TGG ATC AAC CCG GAT CGC AAC CCA GTA CAT GTG GGT CGG GCT ATG    1216
Pro Trp Ile Asn Pro Asp Arg Asn Pro Val His Val Gly Arg Ala Met
365                 370                 375                 380

GTC TTC TCC TTC TCC ACC TTC CAC CTT TAT CTC ACC CTT AAT TTC        1264
Val Phe Ser Ser Phe Thr Phe His Leu Tyr Leu Thr Leu Asn Phe
        385                 390                 395

CTC CTT CCT TTG AAG GTA CTG GAG ATA GCA AAT ACA ATA TTC TGC CAA    1312
Leu Leu Pro Leu Lys Val Leu Glu Ile Ala Asn Thr Ile Phe Cys Gln
400                 405                 410

TGG TTC AAG GGT AAG TAC ATG GAT CTT AAA AGG AAG ACG AGG TTG TTG    1360
Trp Phe Lys Gly Lys Tyr Met Asp Leu Lys Arg Lys Thr Arg Leu Leu
415                 420                 425

TTG CGT TTA GTA GAC ATT TAT AAA CCC TAC CTC TTC TTC CAA GGC ATC    1408
Leu Arg Leu Val Asp Ile Tyr Lys Pro Tyr Leu Phe Phe Gln Gly Ile
430                 435                 440

TTT GAT GAC ATG AAC ACT GAG AAG TTG CGG ATT GCT GCA AAA GAA AGC    1456
Phe Asp Asp Met Asn Thr Glu Lys Leu Arg Ile Ala Ala Lys Glu Ser
445                 450                 455                 460
```

FIGURE 1E

```
ATA GTT GAA GCT GAT ATG TTT TAC TTT GAT CCC AGG GCA ATT AAC TGG   1504
Ile Val Glu Ala Asp Met Phe Tyr Phe Asp Pro Arg Ala Ile Asn Trp
                465                     470                 475

GAA GAT TAC TTC TTG AAA ACT CAT TTC CCA GGN GTC GTA GAG CAC GTT   1552
Glu Asp Tyr Phe Leu Lys Thr His Phe Pro Gly Val Val Glu His Val
                480                     485                 490

CTT AAC TAAAAGTTAC GGTACGAAAA TGAGAAGATT GGAATGCATG CACCGAAAGN    1608
Leu Asn

NCAACATAAA AGACGTGGTT AAAGTCATGG TCAAAAAAGA AATAAAATGC AGTTAGGTTT 1668

GTGTTGCAGT TTTGATTCCT TGTATTGTTA CTTGTACTTT TGATCTTTTT CTTTTTTAAT 1728

GAAATTTCTC TCTTTGTTTT GTGAAAAAAA AAAAAAAAAA GAGCTCCTGC AGAAGCTT   1786
```

FIGURE 1F

WAX ESTERS IN TRANSFORMED PLANTS

This application is a continuation-in-part of U.S. Ser. No. 07/920,430, filed Jul. 31, 1992, now U.S. Pat. No. 5,370,996, which is a continuation-in-part of U.S. Ser. No. 07/796,256 filed Nov. 20, 1991, now abandoned, and a continuation-in-part of U.S. Ser. No. 07/767,251, filed Sep. 27, 1991, now U.S. Pat. No. 5,403,918, and a continuation-in-part of U.S. Ser. No. 07/659,975, now abandoned, filed Feb. 22, 1991.

INTRODUCTION

The present invention is directed to plant enzymes, methods to purify, and obtain such enzymes, amino acid and nucleic acid sequences related thereto, and methods of use for such compositions, particularly in the production of wax esters in a plant cell.

Through the development of plant genetic engineering techniques, it is possible to transform and regenerate a variety of plant species to provide plants which have novel and desirable characteristics. One area of interest for such plant genetic engineering techniques is the production of valuable products in plant tissues. Such applications require the use of various DNA constructs and nucleic acid sequences for use in transformation events to generate plants which produce the desired product. For example, plant functional promoters are required for appropriate expression of gene sequences, such expression being either in the whole plant or in selected plant tissues. In addition, selective marker sequences are often used to identify the transformed plant material. Such plant promoters and selectable markers provide valuable tools which are useful in obtaining the novel plants.

Fatty acids are organic acids having a hydrocarbon chain of from about 4 to 24 carbons. Many different kinds of fatty acids are known which differ from each other in chain length, and in the presence, number and position of double bonds. In cells, fatty acids typically exist in covalently bound forms, the carboxyl portion being referred to as a fatty acyl group. The chain length and degree of saturation of these molecules is often depicted by the formula CX:Y, where "X" indicates number of carbons and "Y" indicates number of double bonds.

Fatty acyl groups are major components of many lipids, and their long, non-polar hydrocarbon chain is responsible for the water-insoluble nature of these lipid molecules. The type of covalent linkage of the fatty acyl group to other factors can vary. For example, in biosynthetic reactions they may be covalently bound via a thioester linkage to an acyl carrier protein (ACP) or to CoenzymeA (CoA), depending on the particular enzymatic reaction. In waxes, fatty acyl groups are linked to fatty alcohols via an ester linkage, and triacylglycerols have three fatty acyl groups linked to a glycerol molecule via an ester linkage.

Many plants have been studied which store lipid as triacylglycerols composed primarily of long chain (having 16 or 18 carbons) fatty acyl groups. Very long chain (having 20–24 carbons) monounsaturated fatty acyl groups are formed by an acyl-CoA elongation pathway from C18:1 and are found in many plant seeds, notably members of the Crucifereae family.

The desert shrub, *Simmondsia chinensis*, better known as jojoba, is unusual among higher plants (seed-bearing plants) in its ability to produce and store large amounts of liquid wax as the major component of its seed storage lipid. These simple wax compounds are oxygen esters of very long-chain monoenoic fatty acyl groups and alcohols (Ohlrogge et al. (*Lipids* (1978) 13:203–210). International Application WO 93/10241, published May 27, 1993, describes methods of expressing a wax synthase in a plant cell in conjunction with a reductase to produce wax esters. In WO 92/14816, published Sep. 3, 1992, the nucleic acid sequence to the jojoba fatty acyl reductase is disclosed.

Many other organisms produce wax esters from alcohol and acyl substrates. For example, plants produce epidermal, or cuticular wax (Kolattukudy (1980) in *The Biochemistry of Plants* (Stumpf, P. K. and Conn, E. E., eds.) Vol.4, p. 571–645). Wax has also been reported for various species of bacteria, such as Acinetobacter (Fixter et al. (1986) *J. Gen. Microbiol.* 132:3147–3157) and Micrococcus (Lloyd (1987) *Microbios* 52:29–37), and by the unicellular organism, Euglena (Khan and Kolattukudy (1975) *Arch. Biochem. Biophys.* 170:400–408). In addition, wax production has been reported in microsomal preparations from bovine meibomian glands (Kolattukudy et al. (1986) *J. Lipid Res.* 27:404–411), avian uropygial glands, and various insect and marine organisms.

The composition and biosynthetic pathway of these waxes may differ from the jojoba seed wax. For jojoba it has been postulated that the reduction of a very long chain fatty acyl-CoA to the corresponding alcohol is dependent upon a single enzyme whose activity has been observed in crude extracts from developing jojoba seeds (Pollard et al. (1979) *Lipids* 14:651–662; Wu et al. (1981) *Lipids* 16:897–902). By comparison, for the formation of plant cuticular waxes, a two step process has been reported (Kolattukudy (1980) in *The Biochemistry of Plants* (Stumpf, P. K. and Conn, E. E., eds.) Vol. 4, p. 571–645). The fatty acyl-CoA is converted to a free aldehyde by the action of an NADH-dependent reductase and the alcohol is subsequently formed by the action of an NADPH-dependent fatty aldehyde reductase.

Solubilization of a multienzyme complex from *Euglena gracilis* having fatty acyl-CoA reductase activity is reported by Wildner and Hallick (Abstract from *The Southwest Consortium Fifth Annual Meeting*, Apr. 22–24, 1990, Las Cruces, N. Mex.). In the formation of Euglena storage wax the alcohol portion is formed by an NADH-dependent reduction of a fatty acyl compound catalyzed by a fatty acyl-CoA reductase.

BRIEF DESCRIPTION OF THE FIGURES

FIG. 1A–F. Nucleic acid sequence and translated amino acid sequence of a jojoba fatty acyl reductase is provided (SEQ ID NO: 19).

SUMMARY OF THE INVENTION

The present invention provides a method for producing wax esters in a plant cell comprising the step of growing a plant cell having a fatty acyl reductase expressed from a sequence heterologous to said plant. Prior to this invention it was not known that wax esters would be produced in a plant cell in the absence of a wax synthase expressed from a sequence which is heterologous to the plant.

Plant cells are preferably grown having a reductase expressed from a recombinant construct which comprises a nucleic acid sequence encoding a jojoba fatty acyl reductase under the control of regulatory elements functional in the plant cell. Cruciferous plant seed cells expressing a jojoba reductase and producing wax esters are exemplified, specifically Brassica and Arabidopsis cells. Thus, the invention may be used to produce wax esters in plant cells which are not known to naturally produce wax esters.

The mechanism by which wax esters are produced in cells expressing the reductase sequence is not known. It may be that plant cells other than jojoba cells contain some activity which is capable of synthesizing wax ester from the fatty alcohol produced by the reductase and a fatty acyl substrate endogenous to the plant cells. Methods for determining plant cells which contain a wax synthesizing capability are also described herein.

The reductase used in the present invention may be active with a variety of fatty acyl substrates, including acyl-CoAs and acyl-ACPs. The carbon chain length of these substrates may vary, although a given reductase may show preference for a specific chain length acyl substrate or may have a wide range of acyl substrates, in terms of preferred carbon chain lengths. The reductase sequence exemplified is a long chain fatty acyl reductase obtainable from jojoba, although methods are provided whereby other fatty acyl reductases may be used to produce wax esters in a plant cell.

The properties of wax esters will vary depending on the chain length and degree of saturation of the fatty alcohol and fatty acyl groups. One ordinarily skilled in the art will recognize that a number of mechanisms exist whereby plant cells may be produced which have a variety of desirable wax ester products. Alteration of the substrates provided by a host plant cell is one mechanism for affecting a change in the wax ester produced by the cell, however, by altering the specificity of the jojoba reductase encoding sequence or by utilizing a reductase encoding sequence from a different source the wax ester produced by the cell may also be varied.

Additionally, it may be necessary to utilize an alternative reductase encoding sequence, for instance where the plant cell does not contain an endogenous long chain fatty acyl substrate of the jojoba reductase, or where a plant host cell does not contain a wax synthesizing capability which is active toward the long chain fatty alcohol produced by the jojoba reductase. Consequently, wax esters having various properties are contemplated by the invention, depending on the substrates presented by the host cell and the activity and the reductase.

Potential sources of reductase encoding sequences may be identified by their ability to produce fatty alcohols or wax esters. Methods are described whereby other sequences may be identified and obtained from the amino acid sequences of the reductase protein exemplified herein. Uses of the structural gene sequences for isolation of other reductase sequences, as well as in recombinant constructs for transcription of reductase nucleic acid sequences and/or expression of reductase proteins in host cells are described. Uses of other nucleic acid sequences associated with reductase protein are also considered, such as the use of 5' and 3' noncoding regions.

In yet a different aspect of this invention, cells containing wax esters of this invention are also considered. Exemplified are cells which contain the preferred substrates of the jojoba reductase, such as those cells in embryos of certain cruciferous plants. Wax esters are present as a component of the total lipids of a seed cell at a level of greater than about 0.5%.

DETAILED DESCRIPTION OF THE INVENTION

Fatty acyl reductase, or "reductase", is active in catalyzing the reduction of a fatty acyl group to the corresponding alcohol. Co-pending U.S. patent application Ser. Nos. 07/659,975 (filed Feb. 22, 1991) (continued as 08/149,007 (filed Nov. 8, 1993)), 07/767,251 (filed Sep. 27, 1991) and 07/920,430 (filed Jul. 31, 1992), which are hereby incorporated by reference, are directed to such reductase proteins. Information regarding jojoba reductase, including the nucleic acid encoding sequences, is also provided in PCT patent application WO 92/14816, published Sep. 3, 1992, which is also incorporated herein by reference. A fatty acyl reductase for use in the present invention includes any sequence of amino acids, such as protein, polypeptide or peptide fragment, which is active in catalyzing the reduction of a fatty acyl group to the corresponding alcohol. By fatty acyl group is intended any fatty acyl group, covalently bound to a carrier, such as ACP or coenzyme A.

By this invention, it has been determined that a heterologous fatty acyl reductase protein can be expressed in a plant cell to cause the production of wax esters. The production of wax esters in the plant cells occurs absent a wax synthase expressed from a sequence heterologous to said plant. While the exemplified cruciferous plant cells have expressed long-chain wax esters by this method, further study of the reductase protein may lead to site-specific mutagenesis studies to further characterize and improve its catalytic properties or to alter its acyl substrate specificity. A reductase with altered substrate specificity may find application in conjunction with other FAS enzymes. For example, a medium chain (C12–C14) preferring plant thioesterase (see copending U.S. patent application Ser. No. 07/662,007), and an appropriate acyl transferase may be used in conjunction with an altered reductase to produce medium-chain alcohols, which may then be converted by a host plant cell to medium chain wax esters by a wax synthesizing activity endogenous to the plant cell.

Furthermore, it is recognized that the methods developed for purification of the jojoba reductase may now be applied to purification of similar membrane associated acyl-CoA reductases from other organisms, which may then similarly be used to produce wax esters in plant host cells. In this manner, a variety of reductases having a range of substrate preferences or specificities may be obtained. Among desirable sources of such reductases are Acinetobacter species, Micrococcus and green algae (Euglena).

Recovery of substantially purified reductase proteins can be accomplished using a variety of methods. For example, polyacrylamide gels may be run and the proteins transferred to a membrane support, such as nitrocellulose or polyvinylidenedifluoride (PVDF). The sections of these membranes which contain the identified proteins may then be obtained such that the identified proteins are substantially free of other proteins. Using techniques known in the art and also described in the following examples, the proteins may be removed from the membranes and further manipulated such that their amino acid sequences are determined.

For example, amino acid sequence can be determined by sequencing N-terminal amino acid regions from whole protein or by preparing fragments of the desired protein by digestion with the chemical cyanogen bromide, or alternatively by enzymatic cleavage using proteases. Examples of proteases which may be useful include endoproteinase lysC, gluC, AspN and trypsin. The fragments obtained in this manner may then be purified and sequenced in accordance with methods familiar to those skilled in the art.

It may also be desirable to express reductase proteins in plant cells in order to provide acyl alcohol products, which have uses in pharmaceuticals, cosmetics, detergents, plastics, and lube oils may be obtained. As described herein, expression of the jojoba reductase in transgenic Brassica and Arabidopsis plants results in the production of long chain wax esters in the seeds of these plants, which are easily converted to the corresponding fatty acyl alcohol and fatty acyl substrates by known saponification or transesterification processes.

In some instances, for example in utilizing alternative sources of reductase, various manipulations may be necessary for expression of reductase activity in cells. For example, leader peptides responsible for membrane insertion may be identified, and constructs prepared which contain only the mature reductase encoding sequence. The reductase nucleic acids of this invention may be genomic or cDNA and may be isolated from cDNA or genomic libraries or directly from isolated plant DNA. Methods of isolation of gene sequences once a protein is isolated and/or amino acid sequence of the protein is obtained are known to those skilled in the art.

For example, antibodies may be raised to the isolated protein and used to screen expression libraries, thus identifying clones which produce the plant acyl reductase protein or an antigenic fragment thereof. Alternatively, oligonucleotides may be synthesized from the amino acid sequences and used in isolation of nucleic acid sequences. The oligonucleotides may be useful in PCR to generate a nucleic acid fragment, which may then be used to screen cDNA or genomic libraries. In a different approach, the oligonucleotides may be used directly to analyze Northern or Southern blots in order to identify useful probes and hybridization conditions under which these oligonucleotides may be used to screen cDNA or genomic libraries.

The acyl reductase nucleic acid sequences exemplified in this invention include those corresponding to the jojoba acyl-CoA reductase protein, as well as sequences obtainable from the jojoba protein or nucleic acid sequences. By "corresponding" is meant nucleic acid sequences, either DNA or RNA, including those which encode jojoba acyl reductase protein or a portion thereof, regulatory sequences found 5' or 3' to said encoding sequences which direct the transcription or transcription and translation (expression) of the reductase in jojoba embryos, intron sequences not present in the cDNA, as well as sequences encoding any leader or signal peptide of a precursor reductase protein that may be required for insertion into the endoplasmic reticulum membrane, but is not found in the mature, or processed, acyl reductase enzyme.

By sequences "obtainable" from the jojoba sequence or protein, is intended any nucleic acid sequences associated with a desired fatty acid reductase protein that may be synthesized from the jojoba acyl reductase amino acid sequence, or alternatively identified in a different organism and isolated using jojoba reductase nucleic acid sequences or antibodies prepared against the jojoba reductase protein as probes. In this manner, it can be seen that sequences of other acyl reductases that are isolated from a desired organism using the jojoba sequences, either by nucleic acid hybridization or antigenic methods, may similarly be used to isolate still other acyl reductases. Such reductases which are derived through seed-plant reductases isolated via jojoba reductase are likewise considered "obtainable" herein.

For isolation of nucleic acid sequences, cDNA or genomic libraries may be prepared using plasmid or viral vectors and techniques well known to those skilled in the art. Useful nucleic acid hybridization and immunological methods that may be used to screen for the desired sequences are also well known to those in the art and are provided, for example in Maniatis, et al. (*Molecular Cloning: A Laboratory Manual*, Second Edition (1989) Cold Spring Harbor Laboratory, Cold Spring Harbor, N.Y.).

Typically, a sequence obtainable from the use of nucleic acid probes will show 60–70% sequence identity between the target sequence and the given sequence encoding acyl reductase enzyme of interest. However, lengthy sequences with as little as 50–60% sequence identity may also be obtained. The nucleic acid probes may be a lengthy fragment of the nucleic acid sequence, or may also be a shorter, oligonucleotide probe. When longer nucleic acid fragments are employed as probes (greater than about 100 bp), one may screen at lower stringencies in order to obtain sequences from the target sample which have 20–50% deviation (i.e., 50–80 sequence homology) from the sequences used as probe. Oligonucleotide probes can be considerably shorter than the entire nucleic acid sequence encoding an acyl reductase enzyme, but should be at least about 10, preferably at least about 15, and more preferably at least about 20 nucleotides. A higher degree of sequence identity is desired when shorter regions are used as opposed to longer regions. It may thus be desirable to identify enzyme active sites where amino acid sequence identity is high to design oligonucleotide probes for detecting homologous genes.

To determine if a related gene may be isolated by hybridization with a given sequence, the sequence is labeled to allow detection, typically using radioactivity, although other methods are available. The labeled probe is added to a hybridization solution, and incubated with filters containing the desired nucleic acids, either Northern or Southern blots (to screen desired sources for homology), or the filters containing cDNA or genomic clones to be screened. Hybridization and washing conditions may be varied to optimize the hybridization of the probe to the sequences of interest. Lower temperatures and higher salt concentrations allow for hybridization of more distantly related sequences (low stringency). If background hybridization is a problem under low stringency conditions, the temperature can be raised either in the hybridization or washing steps and/or salt content lowered to improve detection of the specific hybridizing sequence. Hybridization and washing temperatures can be adjusted based on the estimated melting temperature of the probe as discussed in Beltz, et al. (*Methods in Enzymology* (1983) 100:266–285).

A useful probe and appropriate hybridization and washing conditions having been identified as described above, cDNA or genomic libraries are screened using the labeled sequences and optimized conditions. The libraries are first plated onto a solid agar medium, and the DNA lifted to an appropriate membrane, usually nitrocellulose or nylon filters. These filters are then hybridized with the labeled probe and washed as discussed above to identify clones containing the related sequences.

For immunological screening, antibodies to the jojoba acyl reductase can be prepared by injecting rabbits or mice with the purified protein, such methods of preparing antibodies being well known to those in the art. Either monoclonal or polyclonal antibodies can be produced, although typically polyclonal antibodies are more useful for gene isolation.

To screen desired plant species, Western analysis is conducted to determine that a related protein is present in a crude extract of the desired plant species, that cross-reacts with the antibodies to the jojoba reductase. This is accomplished by immobilization of the plant extract proteins on a membrane, usually nitrocellulose, following electrophoresis, and incubation with the antibody. Many different systems for detection of the antibody/protein complex on the nitrocellulose filters are available, including radiolabeling of the antibody and second antibody/enzyme conjugate systems. Some available systems have been described by Oberfelder (*Focus* (1989) BRL/Life Technologies, Inc. 11:1–5). When cross-reactivity is observed, genes encoding the related proteins are isolated by screening expression libraries representing the desired plant species. Expression libraries can be constructed in a variety of commercially available vectors, including lambda gt11, as described in Maniatis, et al. (supra).

The clones identified as described above using DNA hybridization or immunological screening techniques are then purified and the DNA isolated and analyzed using known techniques. In this manner, it is verified that the clones encode a related acyl reductase protein. Other seed-plant fatty acyl reductases may be obtained through the use of these reductases in the same manner as the jojoba reductase was used.

It will be recognized by one of ordinary skill in the art that acyl reductase nucleic acid sequences of this invention may be modified using standard techniques of site specific mutation or PCR, or modification of the sequence may be accomplished in producing a synthetic nucleic acid sequence. These modified sequences are also considered acyl reductase nucleic acid sequence of this invention. For example, wobble positions in codons may be changed such that the nucleic acid sequence encodes the same amino acid sequence, or alternatively, codons can be altered such that conservative amino acid substitutions result. In either case, the peptide or protein maintains the desired enzymatic activity and is thus considered part of the instant invention.

A nucleic acid sequence of an acyl reductase enzyme of this invention may be a DNA or RNA sequence, derived from genomic DNA, cDNA, mRNA, or may be synthesized in whole or in part. The gene sequences may be cloned, for example, by isolating genomic DNA from an appropriate source, and amplifying and cloning the sequence of interest using a polymerase chain reaction (PCR). Alternatively, the gene sequences may be synthesized, either completely or in part, especially where it is desirable to provide plant-preferred sequences. Thus, all or a portion of the desired structural gene (that portion of the gene which encodes the reductase protein) may be synthesized using codons preferred by a selected host. Host-preferred codons may be determined, for example, from the codons used most frequently in the proteins expressed in a desired host species.

The DNA sequence encoding a fatty acyl reductase of this invention may be combined with foreign DNA sequences in a variety of ways. By "foreign" DNA sequences is meant any DNA sequence which is not naturally found joined to the reductase, including combinations of DNA sequences from the same organism which are not naturally found joined together. For example, it may be desirable to join sequences encoding a transit peptide to reductase sequences of this invention. In this manner, the reductase may be targeted to a chloroplast where fatty acyl substrates, particularly fatty acyl-ACPs are available.

The DNA sequence encoding an acyl reductase of this invention may be employed in conjunction with all or part of the gene sequences normally associated with the reductase. In its component parts, a DNA sequence encoding reductase is combined in a recombinant construct having, in the 5' to 3' direction of transcription, a transcription initiation control region capable of promoting transcription and translation in a host cell, the nucleic acid sequence encoding reductase and a transcription termination region.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the plant enzyme. Among transcriptional initiation regions which have been described are regions from bacterial and yeast hosts, such as *E. coli, B. subtilis, Sacchromyces cerevisiae*, including genes such as beta-galactosidase, T7 polymerase, tryptophan E and the like.

For the most part, the recombinant constructs will involve regulatory regions functional in plants which provide for production of acyl reductase. The open reading frame, coding for the plant reductase or functional fragment thereof will be joined at its 5' end to a transcription initiation regulatory region. Translational initiation regions may also be desirable and may be provided from the 5' non-coding region of the reductase cDNA sequence or from the translational initiation region naturally associated with the transcription initiation region of the construct. Generally, the combination of transcriptional and translational regulatory regions is referred to as a promoter. Numerous promoter regions are available which provide for a wide variety of constitutive or regulatable, e.g., inducible, expression of structural genes in plants.

Among sequences known to be useful in providing for constitutive gene expression in plants are regulatory regions associated with Agrobacterium genes, such as those for nopaline synthase (Nos), mannopine synthase (Mas), or octopine synthase (Ocs), as well as regions coding for expression of viral genes, such as the 35S and 19S regions of cauliflower mosaic virus (CaMV). The term constitutive as used herein does not necessarily indicate that a gene is expressed at the same level in all cell types, but that the gene is expressed in a wide range of cell types, although some variation in abundance is often detectable. Other useful transcriptional initiation regions preferentially provide for transcription in certain tissues or under certain growth conditions, such as those from napin, seed or leaf ACP, the small subunit of RUBISCO, and the like.

The use of all or part of the complete plant acyl reductase gene may variously be desired, namely the 5' upstream non-coding regions (promoter) together with the structural gene sequence and 3' downstream non-coding regions may be employed. For example, as the jojoba reductase cDNA is now known, the promoter associated with the reductase structural gene may be obtained for jojoba genomic DNA using PCR of hybridization techniques. If a different promoter is desired, such as a promoter native to the plant host of interest or a modified promoter, i.e., having transcription initiation regions derived from one gene source and translation initiation regions derived from a different gene source, or enhanced promoters, such as double 35S CaMV promoters, the sequences may be joined together using standard techniques.

For applications when 5' upstream non-coding regions are obtained from other genes regulated during seed maturation, those preferentially expressed in plant embryo tissue, such as ACP and napin-derived transcription initiation control regions, are desired. Such "seed-specific promoters" may be obtained and used in accordance with the teachings of U.S. Ser. No. 07/147,781, filed Jan. 25, 1988 (now U.S. Ser. No. 07/742,834, filed Aug. 8, 1991), and U.S. Ser. No. 07/494, 722 filed on or about Mar. 16, 1990 having a title "Novel Sequences Preferentially Expressed In Early Seed Development and Methods Related Thereto", all of which copending applications are incorporated herein by reference. Transcription initiation regions which are preferentially expressed in seed tissue are considered desirable for fatty alcohol production in order to minimize any disruptive or adverse effects of the Gene product in other plant parts.

Regulatory transcription termination regions may be provided in recombinant constructs of this invention as well. Transcription termination regions may be provided by the DNA sequence encoding the plant acyl reductase or a convenient transcription termination region derived from a different gene source, especially the transcription termination region which is naturally associated with the transcription initiation region. The transcript termination region will typically contain at least about 0.5 kb, preferably about 1–3 kb of sequence 3' to the structural gene from which the termination region is derived.

Plant expression constructs having a plant acyl reductase as the DNA sequence of interest for expression thereof may be employed with a wide variety of plant life, particularly, plant life which produce very long chain fatty acyl-CoA molecules, such as Brassica, and in particular high erucic acid varieties of rapeseed. Other plants of interest produce desirable substrates, such as medium or long chain fatty acyl molecules, and include but are not limited to rapeseed (Canola varieties), Arabidopsis, sunflower, safflower, cotton, Cuphea, soybean, peanut, coconut and oil palms, and corn. Depending on the method for introducing the DNA expression constructs into the host cell, other DNA sequences may be required. Importantly, this invention is applicable to dicotyledyons and monocotyledons species alike and will be readily applicable to new and/or improved transformation and regeneration techniques.

The method of transformation is not critical to the instant invention; various methods of plant transformation are currently available. As newer methods become available to transform crops, they may be directly applied hereunder. For example, many plant species naturally susceptible to Agrobacterium infection may be successfully transformed via tripartite mating or binary vector methods of Agrobacterium mediated transformation. Other sequences useful in providing for transfer of nucleic acid sequences to host plant cells may be derived from plant pathogenic viruses or plant transposable elements. In addition, techniques of microinjection, DNA particle bombardment, electroporation have been developed which allow for the transformation of various monocot and dicot plant species.

In developing the recombinant construct, the various components of the construct or fragments thereof will normally be inserted into a convenient cloning vector which is capable of replication in a bacterial host, e.g., E. coli. Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the recombinant construct will be a structural gene having the necessary regulatory regions for expression in a host and providing for selection of transformant cells. The gene may provide for resistance to a cytotoxic agent, e.g. antibiotic, heavy metal, toxin, etc., complementation providing prototrophy to an auxotrophic host, viral immunity or the like. Similarly, genes encoding enzymes providing for production of a compound identifiable by color change, such as GUS, or luminescence, such as luciferase are useful. Depending upon the different host species into which the expression constructs are introduced, one or more markers may be employed for selection or detection of transformed tissues, where different conditions for selection are used for the different hosts.

When Agrobacterium is utilized for plant transformation, it may be desirable to have the nucleic acid sequences bordered on one or both ends by T-DNA, in particular the left and right border regions, and more particularly, at least the right border region. These border regions may also be useful when other methods of transformation are employed.

Where Agrobacterium or Rhizogenes sequences are utilized for plant transformation, a vector may be used which may be introduced into an Agrobacterium host for homologous recombination with the T-DNA on the Ti- or Ri-plasmid present in the host. The Ti- or Ri- containing the T-DNA for recombination may be armed (capable of causing gall formation), or disarmed (incapable of causing gall formation), the latter being permissible so long as a functional complement of the vir genes, which encode trans-acting factors necessary for transfer of DNA to plant host cells, is present in the transformed Agrobacterium host. Using an armed Agrobacterium strain can result in a mixture of normal plant cells, some of which contain the desired nucleic acid sequences, and plant cells capable of gall formation due to the presence of tumor formation genes. Cells containing the desired nucleic acid sequences, but lacking tumor genes can be selected from the mixture such that normal transgenic plants may be obtained.

In a preferred method where Agrobacterium is used as the vehicle for transforming host plant cells, the expression or transcription construct bordered by the T-DNA border region (s) will be inserted into a broad host range vector capable of replication in E. coli and Agrobacterium, there being broad host range vectors described in the literature. Commonly used is pRK2 or derivatives thereof. See, for example, Ditta, et al., (Proc. Nat. Acad. Sci., U.S.A. (1980) 77:7347–7351) and EPA 0 120 515, which are incorporated herein by reference. Alternatively, one may insert the sequences to be expressed in plant cells into a vector containing separate replication sequences, one of which stabilizes the vector in E. coli, and the other in Agrobacterium. See, for example, McBride and Summerfelt (Plant Mol. Biol. (1990) 14:269–276), wherein the pRiHRI (Jouanin, et al., Mol. Gen. Genet. (1985) 201:370–374) origin of replication is utilized and provides for added stability of the plant expression vectors in host Agrobacterium cells.

Utilizing vectors such as those described above, which can replicate in Agrobacterium is preferred. In this manner, recombination of plasmids is not required and the host Agrobacterium vir regions can supply trans-acting factors required for transfer of the T-DNA bordered sequences to plant host cells.

For transformation of Brassica cells, for example, Agrobacterium transformation methods may be used. One such method is described by Radke et al. (Theor. Appl. Genet. (1988) 75:685–694).

Methods are provided whereby wax synthesizing capability may determined for plant cells. Exemplified are assays of embryos of Brassica (both canola and high erucic acid rapeseed (HEAR)) and Arabadopsis, demonstrating that each contain a wax synthesizing activity, at a low relative level as compared to that determined for jojoba embryos. In this manner any plant can be assayed for detection of an endogenous wax synthesizing activity to determine candidates for wax ester production. Also, preferred substrates of the wax synthesizing activity may be determined and the reductase construct tailored to contain an encoding sequence to a reductase which produces a preferred fatty alcohol substrate of the endogenous wax synthesizing activity or, alternatively, the reductase chosen to enhance the production of a desired wax ester.

The wax synthesizing activity observed in Brassica embryo cells appears to constitute an activity which converts fatty alcohol generated by the expressed jojoba reductase into wax ester. It has not been determined if such activity is responsible for the conversion of fatty alcohol to wax ester in cells transformed by a reductase encoding sequence heterologous to the plant cell. The activity, if responsible, may be either a dedicated enzyme or an enzyme which has another primary activity. For instance, diacylglycerol acyl-transferase (DAGAT) might be capable of approximating the ligase activity.

Expression of the reductase protein in host plant cells which contain preferred substrates of the acyl reductase results in cells having a detectable wax ester component. While crude oil contains wax ester which is detectable by high temperature gas chromatography, in derivatized oil the wax ester is converted back to its fatty alcohol and fatty acyl substrates, thus it is the fatty acyl alcohol component of the ester which is detected.

The invention now being generally described, it will be more readily understood by reference to the following examples, which are included for purposes of illustration only and are not intended to limit the invention unless so stated.

EXAMPLES

Example 1

Acyl-CoA Reductase Assays

Methods to assay for acyl-CoA reductase activity in microsomal membrane preparations or solubilized protein preparations are described.

A. Radiolabeled Material

Long chain [1-$^{14}$C] fatty acids (specific activity 51–56 Ci/mole), namely 11-cis-eicosenoic acid, 13-cis-docosenoic acid and 15-cis-tetracosenoic acid are prepared by the reaction of potassium [$^{14}$C]cyanide with the corresponding alkyl mesylate, followed by the base hydrolysis of the alkyl nitrile to the free fatty acid. The free fatty acids are converted to their methyl esters with ethereal diazomethane, and purified by preparative silver nitrate thin layer chromatography (TLC). The fatty acid methyl esters are hydrolyzed back to the free fatty acids. Radiochemical purity is assessed by three TLC methods: normal phase silica TLC, silver nitrate TLC, and C18 reversed phase TLC. Radiochemical purity as measured by these methods was 92–98%. Long chain [1-$^{14}$C] acyl-CoAs are prepared from the corresponding [1-$^{14}$C] free fatty acids by the method of Young and Lynen (*J. Bio. Chem.* (1969) 244:377), to a specific activity of 10 Ci/mole. Other [1-$^{14}$C] acyl-CoAs, such as [1-$^{14}$C] tetracasenoyl-CoA, were purchased from Amersham (Arlington Heights, Ill.). [1-$^{14}$C]hexadecanal is prepared by the dichromate oxidation of [1-$^{14}$C]hexadecan-1-ol, according to a micro-scale modification of the method of Pletcher and Tate (*Tet. Lett.* (1978) 1601–1602). The product is purified by preparative silica TLC, and stored as a hexane solution at −70° C. until use.

B. Assay for Reductase Activity in a Microsomal Membrane Preparation

1. Assay 1

Reductase activity in a microsomal membrane preparation is measured by incubation of 20 µM [1-$^{14}$C]acyl-CoA (usually tetracosenoyl-CoA, sp. act. 2–5 Ci/mol) with the sample to be assayed and 2 mM NADPH, in a total volume of 0.25 ml. The incubation mixture also contains 10% w/v glycerol, 1 mM DTT, and is buffered with 50 mM HEPES (4-[2-hydroxyethyl]-1-piperazineethane-sulfonic acid) (HEPES, here and as referred to hereafter is added from a 1M stock solution adjusted to pH 7.5).

The assay is started by the addition of acyl-CoA substrate and the incubation is carried out at 30° C. for one hour. The assay is terminated by placing the assay tube on ice and immediately adding 0.25 ml isopropanol:acetic acid (5:1 v/v). Unlabeled wax esters (0.1 mg) and oleyl alcohol (0.1 mg) are added as carriers. The [$^{14}$C] lipids are extracted by the scaled-down protocol of Hara and Radin (*Anal. Biochem.* (1978) 90:420). Six ml of hexane/isopropanol (3:2, v/v) is added to the terminated assay. The sample is vortexed, 2 ml of aqueous sodium sulphate solution (5.5% w/v) is added, and the sample is again vortexed.

2. Assay 2

Reductase activity in a microsomal membrane preparation is measured by incubation of 20 µM [1-$^{14}$C]acyl-CoA (usually tetracosenoyl-CoA, sp. act. 2–5 Ci/mol) with the sample to be assayed and 2 mM NADPH, in a total volume of 0.25 ml. The incubation mixture also contains 10% w/v glycerol, 1 mM DTT, and is buffered with 50 mM HEPES (4-[2-hydroxyethyl]-1-piperazineethane-sulfonic acid) (HEPES, here and as referred to hereafter is added from a 1M stock solution adjusted to pH 7.5). If it is desired to inhibit an acyl CoA: alcohol acyl transferase activity which is also present in the membrane preparation (and which consumes the product of the reductase reaction), 0.3% w/v CHAPS is included in the assay mixture. This concentration of CHAPS has a minimal effect on the reductase enzyme but completely inhibits the acyl transferase reaction, thus simplifying quantitation of the reductase activity.

The assay is started by the addition of acyl-CoA substrate and the incubation is carried out at 30° C. for one hour. The assay is terminated by placing the assay tube on ice and immediately adding 0.25 ml isopropanol:acetic acid (4:1 v/v). Unlabeled wax esters (25 µg), oleyl alcohol (50 µg), and oleic acid (50 µg) are added as carriers. The [$^{14}$C] lipids are extracted by the scaled-down protocol of Hara and Radin (*Anal. Biochem.* (1978) 90:420). Four ml of hexane/isopropanol (3:2, v/v) is added to the terminated assay. The sample is vortexed, 2 ml of aqueous sodium sulphate solution (6.7% w/v) is added, and the sample is again vortexed.

C. Assay for Solubilized Reductase Activity

For assaying solubilized reductase activity, several changes, including the addition of salt for enzyme activation, are required. The assay buffer for a solubilized reductase assay is as indicated above for the microsomal membrane preparation assay, with the following changes:

a. NaCl is added to a final concentration of between 0.3 and 0.5M, b. EDTA is included at ~1 mM, and c. the enzyme sample to be assayed, which typically contains 0.75% CHAPS, is diluted to ≦0.3% (the CMC for CHAPS is ~0.5%).

D. Analysis of Assay Products

For analyzing the products of either the microsomal membrane preparation reductase assay or the solubilized reductase assay, two protocols have been developed. One protocol, described below as "extensive assay" is more time-consuming, but yields more highly quantitative results. The other protocol, described below as "quick assay" also provides a measure of reductase activity, but is faster, more convenient, and less quantitative.

1. Extensive Analysis

Following addition of the sodium sulphate and vortexing the sample, the upper organic phase is removed and the lower aqueous phase is washed with 4 ml hexane/isopropanol (7:2 v/v). The organic phases are pooled and evaporated to dryness under nitrogen. The lipid residue is resuspended in a small volume of heptane, and an aliquot is assayed for radioactivity by liquid scintillation counting. The remainder of the sample can be used either for TLC analysis of the labeled classes, or for derivatization to cleave the wax esters, and thereby give a measure of total alcohol produced.

For lipid class analysis the sample is applied to a silica TLC plate, and the plate is developed in hexane/diethyl ether/acetic acid (such as 80:20:1 or 70:30:1 v/v/v). The distribution of radioactivity between the lipid classes, largely wax esters (when ligase is present, as in the microsomal membrane preparation assay), free fatty acids, fatty alcohols, and polar lipids at the origin, is measured using an AMBIS radioanalytic imaging system (AMBIS Systems Inc., San Diego, Calif.). If necessary the individual lipid classes can be recovered from the TLC plate for further analysis.

For cleavage of the wax esters, a scaled down protocol based on the Grignard derivatization protocol of Pina et al. (*Lipids* (1987) 22:358–361) is used. The sample, plus 200 µg of carrier wax esters, is dried down in a glass tube fitted with a teflon-lined screw cap. Dry diethyl ether (0.4 ml), ethyl acetate (3 µl), and 3M ethyl magnesium bromide in diethyl ether (0.1 ml) are added sequentially. The sample is vortexed and allowed to stand at room temperature for at least 2 hours, after which water-saturated diethyl ether is carefully added to destroy excess reagent. Two ml each of 1M HCl and hexane are added and the tube is vortexed. The upper organic phase is washed with water (2×2 ml) and evaporated to dryness in the presence of 50–100 µl of ethanol.

The sample is resuspended in 50–100 µl of hexane and applied to a TLC plate. Both normal and reversed-phase TLC systems have been used for the analysis. Normal phase TLC uses a silica TLC plate, developed with hexane/diethyl ether/acetic acid (70:30:2 v/v/v). The reversed phase system uses C18 plates developed in methanol.

2. Quick Analysis

Following addition of the sodium sulfate and vortexing the sample, a known percentage of the organic phase is removed and counted via liquid scintillation counting. This calculation is used to estimate the total counts in the organic phase. Another portion of the organic phase is then removed, dryed down under nitrogen, redissolved in heptane and spotted on TLC plates and developed and scanned as described for the detailed assay. In this manner the percentage of the total counts which are incorporated into alcohol is determined.

Example 2

Characterization of Jojoba Acyl-CoA

Reductase

Methods to obtain protein preparations having reductase activity and results of studies of this enzymatic activity are exemplified using jojoba.

A. Seed Development and Acyl-CoA Reductase Activity Profiles

Embryo development was tracked over two summers on five plants in Davis, Calif. Embryo fresh and dry weights were found to increase at a fairly steady rate from about day 80 to about day 130. Lipid extractions reveal that when the embryo fresh weight reaches about 300 mg (about day 80), the ratio of lipid weight to dry weight reaches the maximum level of 50%.

Acyl-CoA reductase activity was measured in developing embryos as described in Example 1. As the jojoba seed coats were determined to be the source of an inhibiting factor(s), the seed coats were removed prior to freezing the embryos in liquid nitrogen for storage at −70° C.

Development profiles for acyl-CoA reductase activities as measured in either a cell free homogenate or a membrane fraction, indicate a large induction in reductase activity which peaks at approximately 115 days after anthesis. Embryos for enzymology studies were thus harvested between about 90 to 110 days postanthesis, a period when the reductase activity is high, lipid deposition has not reached maximum levels, and the seed coat is easily removed. The highest rate of increase of reductase activity is seen between days 80 and 90 postanthesis. Embryos for cDNA library construction were thus harvested between about 80 to 90 days postanthesis when presumably the rate of synthase of reductase protein would be maximal. Correspondingly, the level of mRNA encoding acyl-CoA reductase would be presumed to be maximal at this stage.

B. Fractionation Studies

Early attempts to fractionate jojoba embryo samples resulted in variable distribution of reductase activity in the fat pad, supernatant and particulate fractions resulting from centrifugation. A large number of treatments to potentially affect the distribution of activity were tested, such as sonication, floatation gradients, and the addition of various agents to the extraction buffer. The inclusion of salts in the extraction buffer resulted in the greatest improvement in recovery of ligase activity in the supernatant fraction upon centrifugation at 100,000×g for one hour. The extraction buffer consists of 3M NaCl, 0.3M sucrose, 100 mM HEPES, 2 mM DTT, and the protease inhibitors, 1 mM EDTA, 0.7 mg/ml leupeptin, 0.5 mg/ml pepstatin and 17 mg/ml phenylmethanesulfonyl fluoride (PMSF).

C. Microsomal Membrane Preparations

Particles having high levels of reductase activity can be obtained from the supernatant fraction described above either by dialysis followed by centrifugation at 100,000×g or by ammonium sulphate fractionation. The dialysis method is described in detail in Example 3. Further analysis of these particles having reductase activity such as density gradient centrifugation, gel permeation chromatography, and protein/phospholipid analysis establishes that these particles represent a membrane fraction. This membrane preparation also has high cytochrome C reductase activity, which activity is used as a marker for endoplasmic reticulum (ER) membranes. These studies thus establish that the reductase protein is associated with membranes.

For ammonium sulphate fractionation, the 100,000×g supernatant is obtained from jojoba embryos essentially as described in Example 3. An equal volume of ammonium sulphate solution (33.2 g/100 ml) is slowly added to the supernatant fraction (with stirring) to bring the ammonium sulphate concentration to 30%, a concentration that will effectively precipitate the reductase enzyme. Following 30 additional min. of stirring, the suspension is centrifuged at 26,000×g for 30 min., and the pellet resuspended in one tenth of the volume of the first supernatant fraction, S1, using a solution consisting of 25 mm HEPES, 1M NaCl, 1 mM DTT, 0.1 mM PMSF. The suspension is centrifuged at 100,000×g for one hour, and the resulting pellet resuspended in 25 mM HEPES, 10% glycerol (again at 1/10th of the S1 volume). Centrifugation of this suspension at 100,000×g yields the washed microsomal pellet, P4, which is resuspended in 1/20th of the S1 volume of 25 mM HEPES, 10% glycerol yielding a protein concentration of about 3–4 mg/ml. Aliquots are frozen at −70° C. for later use.

D. Study of Membrane Association of Reductase Activity

The Triton X114 phase fractionation procedure described by Bordier (*J. Biol. Chem.* (1981) 256:1604–1607) is used to determine whether the jojoba reductase is an integral membrane protein, or is more loosely associated with the membrane layer (more highly hydrophilic proteins). This technique essentially involves incubation of the membranes with 1% Triton X114 on ice followed by raising the temperature of the mixture above the cloud point of the detergent under these conditions (the cloud point is the temperature at which very large micelles begin to spontaneously form, for 1% Triton X114 this is ~20° C.). Upon centrifugation, two distinct phases can be observed, a lower detergent rich phase and an upper detergent depleted phase (referred to here as the aqueous phase). Integral membrane proteins have been shown to preferentially partition into the detergent rich phase while more highly hydrophilic proteins are recovered in the aqueous phase. When jojoba membrane preparations are subjected to this Triton X114 phase fractionation protocol, reductase activity is associated with the detergent enriched phase and no reductase activity is detected in the aqueous phase. This is evidence that the reductase enzyme is an integral membrane protein.

E. Further Characterization of Reductase Enzyme

The microsomal membrane preparation described above is used for further characterization of the reductase enzyme. The reductase enzyme was shown to be active over the range of pH 5–9. Characterization experiments were conducted at pH 7.5, which is close to the presumed physiological pH of the cytoplasm.

1. Salt Effects

A variety of salts were examined for their effect on reductase activity using a standard concentration of 0.5M for monobasic salts. Salts with divalent cations or anions were examined at 0.167M (to give the same ionic strength as the 0.5M monobasic salts) and also at 0.5M. Up to 15-fold stimulation is observed with the addition of 0.5M NaCl. Other salts, both monovalent and divalent (such as LiCl, KCl, MgCl$_2$, CaCl$_2$ and Na$_2$SO$_4$) were also shown to stimulate reductase activity, although generally to a lesser degree as compared to the NaCl stimulation. Strongly chaotropic salts, KSCN and NaSCN gave no stimulation or marginal stimulation of reductase activity.

2. Other Effectors

Dithiothreitol (DTT) was found to be stimulatory to reductase activity, but not obligatory, while ethylenediaminetetraacetic acid (EDTA) gave some stimulation, with the optimum concentration being 2.5 mM. A small stimulation of activity was observed at low (0.02–0.075 mg/ml) BSA (bovine serum albumin) concentrations, while inhibition of activity was observed at BSA concentrations at and above 0.2 mg/ml.

Earlier observations that the acyl-CoA reductase is an NADPH specific activity (Pollard et al., supra) were confirmed. No NADH-dependent activity was measurable above background (<2% of the NADPH-dependent activity). Also, both water-soluble end-products of the reductase reaction, CoA and NADP+, give significant inhibition of activity (at millimolar concentrations), while NADH and AND+ have marginal effects on activity.

3. Substrate Specificity

The thioesters of various chain length fatty acids, acyl-ACPs and acyl-CoAs, were compared as substrates for the reductase enzyme. Tests were conducted at substrate concentrations of 10 uM, as the tetracosenoyl-CoA (24:1-COA) substrate shows strong substrate inhibition at greater concentrations. NaCl concentration in these assays is 0.5M. Results of the substrate specificity experiment are presented in Table 1 below.

TABLE 1

| Acyl Specificity of the Reductase | | |
|---|---|---|
| | Reductase Activity (pmoles/min/µl) | |
| Acyl Group | Acyl-ACP (10 µM) | Acyl-CoA (10 µM) |
| 12:0 | <0.01 | <0.15 |
| 16:0 | 2.9 | <0.4 |
| 18:0 | — | 1.4 |
| 18:1 | 1.05 | 0.75 |
| 20:1 | — | 1.0 |
| 22:1 | — | 1.0 |
| 24:1 | — | 19.9 |

Tetracosenoyl-CoA has the highest substrate activity of those tested, and is thus used for reductase assays in further enzyme purification and characterization experiments. Of interest, palmitoyl-CoA (C16:0-CoA) and palmitoyl-ACP (C16:0-ACP) were directly compared as substrates. The activity towards palmitoyl-CoA was barely above background, while activity towards palmitoyl-ACP was high. Previously, stearoyl-ACP (C18:0-ACP) was shown to have activity as a substrate (Pollard et al., supra).

Also of interest, although palmitoyl-CoA appears to be a poor substrate for the reductase enzyme, in a competitive inhibition experiment conducted using unlabelled palmitoyl-CoA (0–30 mM) and [1–14C]tetracosenoyl-CoA (20 mM), 50% inhibition of reductase activity towards tetracosenoyl-CoA occurred at 5 mM palmitoyl-CoA. Thus, although palmitoyl-CoA is a poor substrate under the assay conditions, it is an effective inhibitor.

4. Reductase Inhibitor Assays

Several known inhibitors of other types of reductase proteins were tested for their effect on the jojoba acyl-CoA reductase activity. Mevinolin, which is a strong inhibitor of HMG-CoA reductase (3-hydroxyl-3-methylglutaryl-coenzymeA reductase), only has an effect at relatively high concentrations (100 uM) compared to the concentrations inhibitory to HMG-CoA reductase (Ki of approximately 1 nM). Cerulinen is well known to covalently bind to β-ketoacyl thioester synthases, but has no strong inhibitory effect on the jojoba acyl-CoA reductase.

Sulphydryl blocking agents were also screened for their effect on reductase activity. N-ethylmaleimide was shown to strongly inhibit activity, while para-hydroxymercuribenzoate also has some inhibitory effect, and iodoacetamide has no effect. This evidence leads to the conclusion that the acyl-CoA reductase has an essential sulphydryl group that shows considerable selectivity towards various sulphydryl blocking reagents.

Example 3

Purification of Acyl-CoA Reductase

Methods are described which may be used for isolation of a jojoba membrane preparation having reductase activity, solubilization of reductase activity and further purification of the reductase protein.

A. Microsomal Membrane Preparation

Jojoba embryos are harvested at approximately 90–110 days after flowering, as estimated by measuring water content of the embryos (45–70%). The outer shells and seed coats are removed and the cotyledons quickly frozen in liquid nitrogen and stored at −70° C. for future use. For initial protein preparation, frozen embryos are powdered by pounding in a steel mortar and pestle at liquid nitrogen temperature. In a typical experiment, 70 g of embryos are processed.

The powder is added, at a ratio of 280 ml of solution per 70 g of embryos, to the following high salt solution: 3M NaCl, 0.3M sucrose, 100 mM HEPES, 2 mM DTT, and the protease inhibitors, 1 mM EDTA, 0.7 mg/ml leupeptin, 0.5 mg/ml pepstatin and 17 mg/ml PMSF. A cell free homogenate (CFH) is formed by dispersing the powdered embryos in the buffer with a Polytron tissue homogenizer for approximately 30 seconds. The homogenate is filtered through three layers of Miracloth (CalBioChem, LaJolla, Calif.) and the filtrate is centrifuged at 100,000×g for one hour.

The resulting sample consists of a pellet, supernatant and a floating fat pad. The fat pad is removed and the supernatant fraction is collected and dialyzed overnight (with three changes of the buffering solution) versus a solution containing 1M NaCl, 100 mM HEPES, 2 mM DTT and 1 mM EDTA. The dialyzate is centrifuged at 200,000×g for one hour to yield a pellet, DP2. The pellet is suspended in 25 mM HEPES (pH7.5), 10% (w/v) glycerol, 1 mM EDTA and 0.5M NaCl at approximately 1/20 of the original CFH volume, to yield the microsomal membrane preparation.

Activity is assayed as described in Example 1. Recovery of acyl-CoA reductase activity is estimated at approximately 30% of the original activity in the cell free homogenate. Acyl-CoA reductase activity in this preparation is stable when stored at −70° C.

B. Solubilization of Reductase Protein

Solid CHAPS (3-[(3-cholamidopropyl)-dimethylammonio]-1-propanesulfonate) is added to the microsomal membrane preparation to yield a final concentration of 2% (w/v). The sample is incubated on ice with a slow rocking motion for approximately one hour and then diluted with 25 mM HEPES (pH7.5), 10% glycerol, 0.34M NaCl, 1 mM EDTA to lower the CHAPS concentration to 0.75% and the NaCl to approximately 0.4M. The sample is then centrifuged at 200,000×g for one hour and the supernatant recovered and assayed for reductase activity as described in Example 1. Typically, 85% of the reductase activity from the microsomal membrane preparation is recovered in the supernatant fraction. The solubilized reductase activity is stable when stored at −70° C.

C. Blue A Column Chromatography

A column (1.8—10 cm) with a bed volume of approximately 25 ml is prepared which contains Blue A (Cibacron Blue F3GA; Amicon Division, W.R. Grace & Co.), and the column is equilibrated with Buffer A (25 mM HEPES (pH7.5), 20% (w/v) glycerol, 0.75% CHAPS, 1 mM EDTA) containing 0.4M NaCl. The solubilized reductase preparation described above is loaded on to the Blue A column.

The column is washed with several column volumes of Buffer A containing 0.4M NaCl and is then washed further with Buffer A containing 0.5M NaCl. Greater than 90% of the reductase activity binds to the column, while greater than 85% of other protein passes through. Reductase activity is eluted from the column with Buffer A containing 1.0M NaCl. Fractions are collected and assayed for reductase activity as described in Example 1. Fractions containing reductase activity are pooled and stored at −70° C. Typically, 30–50% of the loaded reductase activity is recovered by elution with the 1.0M NaCl buffer.

D. Size Exclusion Chromatography

The pooled active fractions from the Blue A column are concentrated ~10 fold via ultrafiltration in a pressure cell fitted with a YM30 membrane (Amicon Division, W.R. Grace). Typically, the activity is eluted from the BlueA column in ~90 ml and concentrated to ~8 ml and applied to two Sephacryl S100 columns as follows. Columns (2.5×75 cm) are packed with S100HR medium (Pharmacia LKB Biotechnology, Piscataway, N.J.) and equilibrated with Buffer A containing 0.5M NaCl. The columns are size calibrated with the following protein standards: bovine serum albumin (66 kD), carbonic anhydrase (29 kD), cytochrome C (12.4 kD), and blue dextran (used to determine the void volume). A four ml aliquot of the concentrated sample is applied to each of the S100 columns, which are developed at a linear flow rate of approximately 17 cm/hr. Fractions are collected for ~4 hours and the reductase activity in the fractions is measured as described in Example 1.

Greater than 60% of loaded activity is recovered in one main peak which elutes at an apparent molecular mass of approximately 49 kD. The volume of the pooled active fractions is ~30–35 ml/column.

E. Affinity Chromatography

A column (1.5 cm×~2 cm) is packed with palmitoyl-CoA agarose (Sigma Chemical Co., St. Louis, Mo.) and equilibrated with Buffer B (Buffer A containing 0.1M NaCl). Pooled active fractions from the gel filtration columns are concentrated ~16 fold via ultrafiltration as described above. The NaCl level in the concentrated sample is reduced from 0.5M to ~0.1M by dilution with Buffer A. The diluted sample is applied to the column which is then washed with several column volumes of Buffer B. The column is then washed with 10 ml of Buffer B containing 15 mM NADH, followed by further washing with Buffer B. Reductase activity is eluted by passing 15 ml of 15 mM NADPH in Buffer B through the column. Typically, the material from one gel filtration column at a time is processed on the affinity column, and greater than 70% of the activity applied to the column is recovered by elution with NADPH. The active fractions are pooled and analyzed for reductase activity, protein concentration and polypeptide composition. Protein concentrations are estimated using a commercially available kit (Bio-Rad Laboratories, Inc., Richmond, Calif.) based on the dye binding method described by Bradford (*Analy. Biochem.* (1976) 72:248–254). BSA is used as the reference protein.

F. Purification Table

Protein recovery and reductase activity at each step in a typical purification experiment are presented in Table 2 below.

TABLE 2

Purification of Jojoba Reductase

| Purification Step | Enzyme Activity (nmol/min) | Yield (%) | Protein (mg) | Specific Activity (nmol/min/mg) | Purification (fold) |
|---|---|---|---|---|---|
| Crude Homogenate | 380 | | | | |
| First Supernatant | 164 | 100 | 1172 | 0.1 | 1.0 |
| Microsomal Membranes | 82 | 50 | 77.5 | 1.1 | 7.6 |
| Solubilized Fractions | 64 | 39 | 68.5 | 0.9 | 6.7 |
| Blue A Agarose | 39 | 23.8 | 2.2 | 18.1 | 130 |
| Sephacryl-S100 | 13.4 | 8.2 | 1.7 | 8.1 | 58 |
| Palmitoyl-CoA Agarose | 4.7 | 2.9 | 0.2 | 21.9 | 156 |

G. SDS PAGE Analysis

Polypeptide composition of the sample is analyzed by SDS PAGE (Laemmli, U.K. (1970) *Nature* (London) 227:680–685). The samples are prepared for electrophoresis by adding SDS and dithiothreitol from stock solutions to a final concentration of 2% and 30 mM, respectively. Approximately 50 μl of the sample is loaded onto the well of an acrylamide gel having a 12% separating gel (NOVEX, San Diego, Calif.). Molecular mass standards were purchased from Bio-Rad Laboratories. Protein is detected by silver staining (Blum et al., *Electrophoresis* (1987) 8:93–99).

Two prominent polypeptide bands having apparent molecular masses of approximately 52 and 54 kD are detected in the active sample from the affinity column which together represent >95% of the protein in this preparation. Further analyses of these samples using a protein size marker system that incudes a 55 kD protein standard results in alternative molecular mass estimates of 54 kD and 56 kD. As the apparent size of the reductase enzyme in the native state is approximately 49 kD (as determined by size exclusion chromatography and described above), these bands likely represent related forms of the reductase enzyme rather than two different subunits of one enzyme.

H. Blotting Proteins to Membranes

The above described reductase polypeptides are further isolated for amino acid sequencing by transfer of these proteins to either nitrocellulose or PVDF, either Immobilon-P (Millipore; Bedford, Mass.) or ProBlott (Applied Biosystems; Foster City, Calif.), membranes following SDS-PAGE. Nitrocellulose is preferred when proteins will be subsequently enzymatically digested, while PVDF is useful for N-terminal sequencing methods and for sequencing of peptides resulting from cyanogen bromide digestion.

1. Blotting to Nitrocellulose

When protein is electroblotted to nitrocellulose, the blotting time is typically 1–5 hours in a buffer such as 25 mM Tris, 192 mM glycine in 5–20% methanol. Following electroblotting, membranes are stained in 0.1% (w/v) Ponceau S in 1% (v/v) acetic acid for 2 minutes and destained in 2–3 changes of 0.1% (v/v) acetic acid, 2 minutes for each change. These membranes are then stored wet in heat-sealed plastic bag at −20° C. If time permits, blots are not frozen but used immediately for digestion to create peptides for determination of amino acid sequence as described below.

2. Blotting to PVDF

When protein is electroblotted to Immobilon P PVDF, the blotting time is generally about 1–2 hours in a buffer such as 12.5 mM Tris/5 mM glycine in 10% (v/v) methanol. Following electroblotting to PVDF, membranes are stained in 0.1% (w/v) Coomassie Blue in 50% (v/v) methanol/10% (v/v) acetic acid for 5 minutes and destained in 2–3 changes of 50% (v/v) methanol/10% (v/v) acetic acid, 2 minutes for each change. PVDF membranes are then allowed to air dry for 30 minutes and are then stored dry in heat-sealed plastic bags at −20° C. Protein blotted to PVDF membranes such as Pro Blott, may be used directly to determine N-terminal sequence of the intact protein. A protocol for electroblotting proteins to ProBlott is described below in Example 4A.

Example 4

Determination of Amino Acid Sequence

In this Example, methods for determination of amino acid sequences of plant proteins associated with acyl-CoA reductase activity are described.

A. Cyanogen Bromide Cleavage of Protein and Separation of Peptides

Cyanogen bromide cleavage is performed on the protein of interest using the methodology described in the Probe-Design Peptide Separation System Technical Manual from Promega, Inc. (Madison, Wis.). The reductase proteins are blotted to a PVDF membrane as described above. Protein bands are cut from the blot, placed in a solution of cyanogen bromide in 70% (v/v) formic acid, and incubated in this solution overnight at room temperature. Following this incubation the cyanogen bromide solutions are removed, pooled and dried under a continuous nitrogen stream using a Reacti-Vap Evaporator (Pierce, Rockford, Ill.). Additional elution of cyanogen bromide peptides may be conducted to ensure complete removal, using a peptide elution solvent such as 70% (v/v) isopropanol, 0.2% (v/v) trifluoroacetic acid, 0.1 mM lysine, and 0.1 mM thioglycolic acid. The elution solvents are then removed and added to the tube containing the dried cyanogen bromide solution, and dried as described above. The elution procedure may be repeated with fresh elution solvent. 50 μl of HPLC grade water is then added to the dried peptides and the water removed by evaporation in a Speed-Vac (Savant, Inc., Farmingdale, N.Y.).

Peptides are separated using a Tris/Tricine SDS-PAGE system similar to that described by Schägger and von Jagow (*Anal. Biochem.* (1987) 166:368–379). Gels are run at a constant voltage of 125–150 volts for approximately 1 hour or until the tracking dye has begun to run off the bottom edge of the gel. Gels are soaked in transfer buffer (125 mM Tris, 50 mM glycine, 10% (v/v) methanol) for 15–30 minutes prior to transfer. Gels are blotted to ProBlott sequencing membranes (Applied Biosystems, Foster City, Calif.) for 2 hours at a constant voltage of 50 volts. The membranes are stained with Coomassie blue (0.1% in 50% (v/v) methanol/10% (v/v) acetic acid) and destained for 3×2 min. in 50% (v/v) methanol/10% (v/v) acetic acid. Membranes are air-dried for 30–45 minutes before storing dry at −20° C.

Peptides blotted on to ProBlott can be directly loaded to the sequencer cartridge of the protein sequencer without the addition of a Polybrene-coated glass fibre filter. Peptides are sequenced using a slightly modified reaction cycle, BLOT-1, supplied by Applied Biosystems. Also, solution S3 (butyl chloride), is replaced by a 50:50 mix of S1 and S2 (n-heptane and ethyl acetate). These two modifications are used whenever samples blotted to ProBlott are sequenced.

B. Protease Digestion and Separation of Peptides

Proteins blotted to nitrocellulose may be subjected to digestion with proteases in order to obtain peptides for sequencing. The method used is that of Aebersold, et al. (*PNAS* (1987) 84:6970). Bands of the reductase proteins, and also an equal amount of blank nitrocellulose to be used as a control, are cut out of the nitrocellulose membrane and washed several times with HPLC grade water in order to remove the Ponceau S. Following this wash, 1.0 ml of 0.5% polyvinylpyrrolidone (PVP-40, Aldrich, Milwaukee, Wis.) in 0.5% acetic acid is added to the membrane pieces and this mixture is incubated for 30 minutes at 37° C. In order to remove the PVP-40 completely, nitrocellulose pieces are washed with many volumes of HPLC grade water (8×5 ml), checking the absorbance of the washes at 214 nm on a spectrophotometer. Also, PVP-40 is more easily removed if bands are not cut into small pieces until after PVP-40 treatment and washing. These two modifications eliminate interference problems with the PVP-40.

The pieces are then suspended in an appropriate digest buffer, for example trypsin digest buffer, 100 mM sodium bicarbonate pH 8.2, or endoproteinase gluC buffer, 25 mM ammonium carbonate/1 mM EDTA, pH 7.8. Acetonitrile is added to the digest mixture to a concentration of 5–10% (v/v). Protease are diluted in digest buffer and added to the digest mixture, typically at a ratio of 1:10 (w/w) protease to protein. Digests are incubated 18–24 hours. For example, trypsin digests are incubated at 37° C. and endoproteinase gluC digests are incubated at room temperature. Similarly, other proteases may be used to digest the reductase proteins, including lysC and aspN. While the individual digest buffer conditions may be different, the protocols for digestion, peptide separation, purification and sequencing are substantially the same as those described for digestion with trypsin and gluC.

Following overnight incubation, digest reactions are stopped by the addition of 10 ml 10% (v/v) trifluoroacetic acid (TFA) or 1 μl 100% TFA. The digest mixture is removed from the nitrocellulose pieces, the nitrocellulose pieces are washed with 1–5 100 ml volumes of digest buffer with 5–10% acetonitrile, and these volumes are concentrated to a volume of less than 100 ml in a Speed-Vac. The peptides are separated on a Vydac reverse phase C18 column (2.1 mm×100 mm) installed in an Applied Biosystems (Foster City, Calif.) Model 130 High Performance Liquid Chromatograph (HPLC). Mobile phases used to elute peptides are: Buffer A: 0.1 mM sodium phosphate, pH2.2; Buffer B: 70% acetonitrile in 0.1 mM sodium phosphate, pH2.2. A 3-step gradient of 10–55% buffer B over two hours, 55–75% buffer B over 5 minutes, and 75% buffer B isocratic for 15 minutes at a flow rate of 50 ml/minute is used. Peptides are detected at 214 nm, collected by hand, and then stored at −20° C.

C. N-terminal Sequencing of Proteins and Peptides

All sequencing is performed by Edman degradation on an Applied Biosystems 477A Pulsed-Liquid Phase Protein Sequencer; phenylthiohydantoin (PTH) amino acids produced by the sequencer are analyzed by an on-line Applied Biosystems 120A PTH Analyzer. Data are collected and stored using an Applied BioSystems model 610A data analysis system for the Apple Macintosh and also on to a Digital Microvax using ACCESS*CHROM software from PE NELSON, Inc. (Cupertino, Calif.). Sequence data is read from a chart recorder, which receives input from the PTH Analyzer, and is confirmed using quantitative data obtained from the model 610A software. All sequence data is read independently by two operators with the aid of the data analysis system.

For peptide samples obtained as peaks off of an HPLC, the sample is loaded on to a Polybrene coated glass fiber filter (Applied Biosystems, Foster City, Calif.) which has been subjected to 3 pre-cycles in the sequencer. For peptides which have been reduced and alkylated, a portion of the PTH-amino acid product material from each sequencer cycle is counted in a liquid scintillation counter. For protein samples which have been electroblotted to Immobilon-P, the band of interest is cut out and then placed above a Polybrene coated glass fiber filter, pre-cycled as above and the reaction cartridge is assembled according to manufacturer's specifications. For protein samples which have been electroblotted to ProBlott, the glass fiber filter is not required.

In order to obtain protein sequences from small amounts of sample (5–30 pmoles), the 477A conversion cycle and the 120A analyzer as described by Tempst and Riviere (*Anal. Biochem.* (1989) 183:290).

D. Amino Acid Sequence of Reductase Peptides

Purified reductase preparations are applied to SDS-PAGE to separate the 54 kD and 56 kD proteins. The separated material is transferred to a nitrocellulose type of membrane (Immobilon N) and stained with Ponceau Red to locate the bands. Excised portions of the blots, containing either the 56 or the 54 kD protein, are treated with trypsin and the tryptic peptides separated by reverse phase HPLC. Sequence information obtained from several peptides (SEQ ID NOS: 1–18) from each reductase protein is presented below in Table 3.

TABLE 3

Peptide Sequences of 54kD and 56kD Reductase Proteins 56 kD Reductase Peptides

1) AILVTGATGSLAK (SEQ ID NO: 1)
2) LQNExFGKELFK (SEQ ID NO: 2)
3) VTVVPGDITGEDL (SEQ ID NO: 3)
4) LGLDINVEK (SEQ ID NO: 4)
5) TIDNVPVYYGK (SEQ. ID NO: 5)
6) YVEPVTYHVGSSAANPM (SEQ ID NO: 6)
7) LSALPEMAHR (SEQ ID NO: 7)
8) LVDIYK (SEQ ID NO: 8)
9) EGIVEADMFYFD (SEQ ID NO: 9)
10) AINWEDYFLKTxFPGVVExVL (SEQ ID NO: 10)

54 kD Reductase Peptides

1) AILVTGATGSLAK (SEQ ID NO: 11)
2) LGLDINVEK (SEQ ID NO: 12)
3) TIDNVPVYYG (SEQ ID NO: 13)
4) YVEPVTYxVGSSAAN (SEQ ID NO: 14)
5) LVDIYKp (SEQ ID NO: 15)
6) EGIVEADMFYF (SEQ ID NO: 16)
7) AINWEDYFL (SEQ ID NO: 17)
8) THFPGVVEHVL (SEQ ID NO: 18)

Peptide sequences are listed using the standard one letter code for amino acids. An "x" indicates that the amino acid at that position was not identified. Amino acid designations which appear in small letters indicate that the identification was tentative for that amino acid.

The similarity of the two reductase proteins is evident from the above peptide sequences. All the peptides from the 54 kD protein are also found in the sequenced 56 kD peptides. There is one discrepancy between the determined amino acid sequences and that reductase amino acid sequence deduced from the cDNA encoding the 56 kD reductase (FIG. 1 (SEQ ID NO: 19)). Amino acid 460 is a serine according to cDNA sequence data. Information from 54 kD and 56 kD peptides 6 and 9, respectively, indicate that a glycine is at this position.

E. Western Analysis

A portion of the reductase cDNA (Example 5) which encodes amino acids 167-235 of the reductase 56 kD protein (see FIG. 1) is ligated into an *E. coli* pGEX expression vector (AMRAD; Burwood, Victoria; Australia) in frame for expression of the reductase peptide from the Taq promoter. The resulting construct is used to transform *E. coli* cells for production of the reductase peptide. The 69 amino acid peptide produced in this manner is purified (Smith et al. (1988) *Gene* 67:31-40) and used to obtain polyclonal antibody to the reductase peptide.

A Western blot of a purified reductase preparation containing the 56 and 54 kD bands and a jojoba cell free homogenate (Example 3A) is prepared for analysis of the reductase preparations using the above described antibody preparation. The 56 kD band is detected in both the cell free homogenate and the purified reductase preparations, while the 54 kD band is detected only in the purified reductase preparation. These results suggest that the 54 kD band observed in the purified reductase preparation is a breakdown product of the 56 kD protein that results from the reductase purification procedure.

Furthermore, Southern blot analysis of restriction enzyme digested jojoba genomic DNA, using four different restriction enzymes, results in detection of one major band and one minor band which hybridize to the reductase cDNA (Example 5) probe.

Example 5

Jojoba Reductase cDNA

A. Jojoba RNA Isolation

RNA is isolated from polyribosomes by a method initially described by Jackson and Larkins (*Plant Physiol.* (1976) 57:5-10) as modified by Goldberg et al. (*Developmental Biol.* (1981) 83:201-217). In this procedure all steps, unless specifically stated, are carried out at 4° C. 10 gm of jojoba embryos collected at 80-90 days post-anthesis are ground in liquid nitrogen in a Waring blender until the tissue becomes a fine powder. After the liquid nitrogen has evaporated, 170 ml of extraction buffer (200 mM Tris pH 9.0, 160 mM KCl, 25 mM EGTA, 70 mM MgCl2, 1% Triton X-100, 0.5% sodium deoxycholate, 1 mM spermidine, 10 mM β-mercaptoethanol, and 500 mM sucrose) is added and the tissue is homogenized for about 2 minutes. The homogenate is filtered through sterile miracloth and centrifuged at 12,000×g for 20 minutes. The supernatant is decanted into a 500 ml sterile flask, and 1/19 volume of a 20% detergent solution (20% Brij 35, 20% Tween 40, 20% Noidet p-40 w/v) is added at room temperature. The solution is stirred at 4° C. for 30 minutes at a moderate speed and the supernatant is then centrifuged at 12,000×g for 30 minutes.

About 30 ml of supernatant is aliquoted into sterile Ti 60 centrifuge tubes and underlaid with 7 ml of a solution containing 40 mM Tris pH 9.0, 5 mM EGTA, 200 mM KCl, 30 mM MgCl2, 1.8M sucrose, 5 mM β-mercaptoethanol. The tubes are filled to the top with extraction buffer, and spun at 60,000 rpm for 4 hours at 4° C. in a Ti60 rotor. Following centrifugation, the supernatant is aspirated off and 0.5 ml of resuspension buffer (40 mM Tris pH 9.0, 5 mM EGTA, 200 mM KCl, 30 mM MgCl$_2$, 5 mM β-mercaptoethanol) is added to each tube. The tubes are placed on ice for 10 minutes, after which the pellets are thoroughly resuspended and pooled. The supernatant is then centrifuged at 120×g for 10 minutes to remove insoluble material. One volume of self-digested 1 mg/ml proteinase K in 20 mM Tris pH 7.6, 200 mM EDTA, 2% N-laurylsarcosinate is added to the supernatant and the mixture incubated at room temperature for 30 minutes.

RNA is precipitated by adding 1/10 volume of sodium acetate and 2 volumes of ethanol. After several hours at −20° C. RNA is pelleted by centrifugation at 12,000×g at 4° C. for 30 minutes. The pellet is resuspended in 10 ml of TE buffer (10 mM Tris, 1 mM EDTA) and extracted with an equal volume of Tris pH 7.5 saturated phenol. The phases are separated by centrifuging at 10,000×g for 20 minutes at 4° C. The aqueous phase is removed and the organic phase is re-extracted with one volume of TE buffer. The aqueous phases are then pooled and extracted with one volume of chloroform. The phases are again separated by centrifugation and the aqueous phase ethanol precipitated as previously described, to yield the polyribosomal RNA.

Polysaccharide contaminants in the polyribosomal RNA preparation are removed by running the RNA over a cellulose column (Sigma-cell 50) in high salt buffer (0.5M NaCl, 20 mM Tris pH 7.5, 1 mM EDTA, 0.1% SDS). The contaminant binds to the column and the RNA is collected in the eluant. The eluant fractions are pooled and the RNA is ethanol precipitated. The precipitated total RNA is then resuspended in a smaller volume and applied to an oligo d(T) cellulose column to isolate the polyadenylated RNA.

B. cDNA Library Construction in a Plasmid Vector

Polyadenylated RNA is used to construct a cDNA library in the plasmid cloning vector pCGN1703, derived from the commercial cloning vector Bluescribe M13- (Stratagene Cloning Systems; San Diego, Calif.), and made as follows. The polylinker of Bluescribe M13- is altered by digestion with BamHI, treatment with mung bean endonuclease, and blunt-end ligation to create a BamHI- deleted plasmid, pCGN1700. pCGN1700 is digested with EcoRI and SstI (adjacent restriction sites) and annealed with a synthetic linker having restriction sites for BamHi, PstI, XbaI, ApaI and SmaI, a 5' overhang of AATT, and a 3' overhang of TCGA. The insertion of the linker into pCGN1700 eliminates the EcoRI site, recreates the SstI (also, sometimes referred to as "SacI" herein) site found in Bluescribe, and adds the new restriction sites contained on the linker. The resulting plasmid pCGN1702, is digested with HindIII and blunt-ended with Klenow enzyme; the linear DNA is partially digested with PvuII and ligated with T4 DNA ligase in dilute solution. A transformant having the lac promoter region deleted is selected (pCGN1703) and is used as the plasmid cloning vector.

Briefly, the cloning method for cDNA synthesis is as follows. The plasmid cloning vector is digested with SstI and homopolymer T-tails are generated on the resulting 3'-overhang stick-ends using terminal deoxynucleotidyl transferase. The tailed plasmid is separated from undigested or un-tailed plasmid by oligo(dA)-cellulose chromatography. The resultant vector serves as the primer for synthesis of cDNA first strands covalently attached to either end of the vector plasmid. The cDNA-mRNA-vector complexes are treated with terminal transferase in the presence of deoxyguanosine triphosphate, generating G-tails at the ends of the cDNA strands. The extra cDNA-mRNA complex, adjacent to the BamHI site, is removed by BamHI digestion, leaving a cDNA-mRNA-vector complex with a BamHI stick-end at one end and a G-tail at the other. This complex is cyclized using an annealed synthetic cyclizing linker which has a 5' BamHI sticky-end, recognition sequences for restriction enzymes NotI, EcoRI and SstI, and a 3' C-tail end. Following ligation and repair the circular complexes are transformed into E. coli strain DH5a (BRL, Gaithersburg, Md.) to generate the cDNA library. The jojoba embryo cDNA bank contains between approximately $1.5 \times 10^6$ clones with an average cDNA insert size of approximately 500 base pairs.

C. cDNA Library Construction in a Lambda Vector

Jojoba polyadenylated RNA is also used to construct a cDNA library in the cloning vector 1ZAPII/EcoRI (Stratagene, San Diego, Calif.). The library is constructed using protocols, DNA and bacterial strains as supplied by the manufacturer. Clones are packaged using Gigapack Gold packaging extracts (Stratagene), also according to manufacturer's recommendations. The cDNA library constructed in this manner contains approximately $1 \times 10^6$ clones with an average cDNA insert size of approximately 400 base pairs.

D. Isolation of Reductase cDNA

PCR techniques with primers designed from reductase peptide sequences are utilized to generate an approximately 1 kb portion of a reductase nucleic acid sequence for screening the jojoba library in the pCGN1703 bacterial vector.

The library is screened using techniques known in the art, such as described in Maniatis et al. (supra). A clone, pCGN7571, for the 56 kD reductase protein is obtained and the DNA sequence determined. Nucleic acid and deduced amino acid sequences of pCGN7571 (SEQ ID NO:19) are presented in FIG. 1.

E. Expression of Reductase cDNA in E. coli pCGN7571 is in vitro mutagenized to introduce an NdeI site at the first ATG of the reductase coding sequence and a BglII site immediately upstream of the NdeI site. BamHI linkers are introduced into the SphI site downstream of the reductase coding region. The 1.5 kb BglII-BamHI fragment is gel purified and cloned into BglII-BamHI digested pCGN3686 (see below), resulting in pCGN7582.

pCGN3686 is a cloning vector derived from Bluescript KS+ (Stratagene Cloning Systems; San Diego, Calif.), but having a chloramphenicol resistance gene and a modified linker region. The source of the chloramphenicol resistance gene, pCGN565 is a cloning vector based on pUC12-cm (K. Buckley Ph.D. Thesis, Regulation and expression of the phi X174 lysis gene, University of California, San Diego, 1985), but containing pUC18 linkers (Yanisch-Perron, et al., *Gene* (1985) 53:103–119). pCGN565 is digested with HhaI and the fragment containing the chloramphenicol resistance gene is excised, blunted by use of mung bean nuclease, and inserted into the EcoRV site of Bluescript KS– (Stratagene: La Jolla, Calif.) to create pCGN2008. The chloramphenicol resistance gene of pCGN2008 is removed by EcoRI/HindIII digestion. After treatment with Klenow enzyme to blunt the ends, the fragment is ligated to DraI digested Bluescript KS+. A clone that has the DraI fragment containing ampicillin resistance replaced with the chloramphenicol resistance is chosen and named pCGN2015. The linker region of pCGN2015 is modified to provide pCGN3686, which contains the following restriction digestion sites, 5' to 3' in the lacZ linker region: PstI, BglII, XhoI, HincII, SalI, HindIII, EcoRV, EcoRI, PstI, SmaI, BamHI, SpeI, XbaI and SacI.

As the BamHI site downstream of the reductase gene is destroyed during construction of pCGN7582, BamHI linkers are inserted into pCGN7582 at the XbaI vector site downstream of the reductase gene, and the NdeI-BamHI fragment containing the reductase gene cloned into BamHI-NdeI digested pET3A (Studier et al. (1990) *Methods Enzymol.* 185:60–89). This plasmid is designated pCGN7800. pCGN7800 is transformed into E. coli BL21 (Studier et al., supra), which has the T7 RNA polymerase under the control of an inducible promoter.

BL21 E. coli cells containing the reductase construct, BL21(pCGN7800), are compared to control BL21 cells having only the pET3A vector. Cultures are grown overnight in ECLB with 40 µg/ml carbenicillin, diluted 1/10 in fresh ECLB with 40 µg/ml carbenicillin and grown for 1 hour. IPTG is added to 1 mM and the cells are grown for 3 additional hours before harvesting. The cells are harvested by centrifugation and the cell pellet stored at −70° C. Cells are broken in a french press and the protein extract is assayed for reductase activity using the reductase assay described in Example 1C, except that the concentration of NADPH is increased from 2 mM to 5 mM. The assay products are analyzed as described in Example 1D. Thin layer chromatography (TLC) analysis of assay products of BL21(pCGN7800) cell extracts reveals alcohol formation, while the extracts from BL21(pET3A) control cells do not catalyze alcohol formation. In addition, SDS PAGE analysis of BL21(pCGN7800) and BL21(pET3A) cells reveals that the 56 kD protein is present in the BL21(pCGN7800) cells and absent from the BL21(pET3A) cells.

To determine if the reductase expressing E. coli cells are producing alcohol, total lipids are extracted from BL21 (pCGN7800) cells and control cells by hexane:isopropanol (3:2) extraction (overnight on a shaker). The organic phase is evaporated to dryness and the lipids are dissolved in a small volume of hexane, analyzed by TLC, and visualized by iodine staining. This analysis indicates that lipids extracted from BL21(pCGN7800) cells contain alcohols, while the lipids extracted from the control cells do not.

To determine the carbon chain length of the alcohol produced in the BL21(pCGN7800) cells, the alcohol band is scraped from TLC plates and analyzed by reverse phase TLC and gas chromatography (GC). GC analysis is conducted as described by Pina et al. (*Lipids* (1987) 22:358–361) using a 30 m SUPELCOWAX™10 (Supelco, Inc.; Bellefonte, Pa.) fused capillary column (0.32 mm internal diameter; 0.2 mm film thickness). The program parameters are as follows: 190° C. for 15 minutes followed by a 5° per minute temperature ramp to 250° C., hold at 250° C. for 3 minutes. In this manner, it is determined that 16:0 and 18:1 alcohols are the predominant alcohols produced in E. coli as the result of expression of the jojoba reductase. No waxes are detected in the transformed E. Coli, which apparently does not contain an endogenous wax synthesizing activity which is active towards these fatty alcohol substrates.

Example 6

Constructs for Plant Expression

A. Expression Cassettes

Expression cassettes which contain 5' and 3' regulatory regions from genes expressed preferentially in seed tissues may be prepared from napin, Bce4 and ACP genes as described, for example in WO 92/03564.

For example, napin expression cassettes may be prepared as follows. A napin expression cassette, pCGN1808, which may be used for expression of wax synthase or reductase gene constructs is described in Kridl et al. (*Seed Science Research* (1991) 1:209–219), which is incorporated herein by reference.

Alternatively, pCGN1808 may be modified to contain flanking restriction sites to allow movement of only the expression sequences and not the antibiotic resistance marker to binary vectors such as pCGN1557 (McBride and Summerfelt, supra). Synthetic oligonucleotides containing KpnI, NotI and HindIII restriction sites are annealed and ligated at the unique HindIII site of pCGN1808, such that only one HindIII site is recovered. The resulting plasmid, pCGN3200 contains unique HindIII, NotI and KpnI restriction sites at the 3'-end of the napin 3'-regulatory sequences as confirmed by sequence analysis.

The majority of the napin expression cassette is subcloned from pCGN3200 by digestion with HindIII and SacI and ligation to HindIII and SacI digested pIC19R (Marsh, et al. (1984) *Gene* 32:481–485) to make pCGN3212. The extreme 5'-sequences of the napin promoter region are reconstructed by PCR using pCGN3200 as a template and two primers flanking the SacI site and the junction of the napin 5'-promoter and the pUC backbone of pCGN3200 from the pCGN1808 construct. The forward primer contains ClaI, HindIII, NotI, and KpnI restriction sites as well as nucleotides 408–423 of the napin 5'-sequence (from the EcoRV site) and the reverse primer contains the complement to napin sequences 718–739 which include the unique SacI site in the 5'-promoter. The PCR is performed using a Perkin Elmer/Cetus thermocycler according to manufacturer's specifications. The PCR fragment is subcloned as a blunt-ended fragment into pUC8 (Vieira and Messing (1982) *Gene* 19:259–268) and digested with HincII to give pCGN3217. Sequence of pCGN3217 across the napin insert verifies that no improper nucleotides were introduced by PCR. The napin 5-sequences in pCGN3217 are ligated to the remainder of the napin expression cassette by digestion with ClaI and SacI and ligation to pCGN3212 digested with ClaI and SacI. The resulting expression cassette pCGN3221, is digested with HindIII and the napin expression sequences are gel purified away and ligated to pIC20H (Marsh, supra) digested with HindIII. The final expression cassette is pCGN3223, which contains in an ampicillin resistant background, essentially identical 1.725 napin 5' and 1.265 3' regulatory sequences as found in pCGN1808. The regulatory regions are flanked with HindIII, NotI and KpnI restriction sites and unique SalI, BglII, PstI, and XhoI cloning sites are located between the 5' and 3' noncoding regions.

Similarly, a cassette for cloning of sequences for transcription regulation under the control of 5' and 3' regions from an oleosin gene may be prepared. Sequence of a *Brassica napus* oleosin gene is reported by Lee and Huang (*Plant Phys.* (1991) 96:1395–1397). Primers to the published sequence are used in PCR reactions to obtain the 5' and 3' regulatory regions of an oleosin gene from *Brassica napus* cv. Westar. Two PCR reactions are performed, one to amplify approximately 950 nucleotides upstream of the ATG start codon for the oleosin gene, and one to PCR amplify approximately 600 bp including and downstream of the TAA stop codon for the oleosin gene. The PCR products are cloned into plasmid vector pAMP1 (BRL) according to manufacturers protocols to yield plasmids pCGN7629 which contains the oleosin 5' flanking region and pCGN7630 which contains the 3' flanking region. The PCR primers included convenient restriction sites for cloning the 5' and 3' flanking regions together into an expression cassette. A PstI fragment containing the 5' flanking region from pCGN7629 is cloned into PstI digested pCGN7630 to yield plasmid pCGN7634. The BssHII (New England BioLabs) fragment from pCGN7634, which contains the entire oleosin expression cassette is cloned into BssHII digested pBCSK+ (Stratagene) to provide the oleosin cassette in a plasmid, pCGN7636. Sequence of the oleosin cassette in pCGN7636 is provided in FIG. 4. The oleosin cassette is flanked by BssHII, KpnI and XbaI restriction sites, and contains SalI, BamHI and PstI sites for insertion of wax synthase, reductase, or other DNA sequences of interest between the 5' and 3' oleosin regions.

The gene sequences are inserted into such cassettes to provide expression constructs for plant transformation methods. For example, such constructs may be inserted into binary vectors for Agrobacterium-mediated transformation as described below.

B. Vectors for Plant Transformation

Binary vectors are prepared from pCGN1578, pCGN1559 and other vectors described by McBride et al. (supra) by substitution of the pCGN1578 and pCGN1559 linker regions with a linker region containing the following restriction digestion sites:
Asp718/AscI/PacI/XbaI/BamHI/SwaI/Sse8387 (PstI)/ HindIII. This results in pCGN1578PASS or pCGN1559PASS, and other modified vectors which are designated similarly. AscI, PacI, SwaI and Sse8387 have 8-base restriction recognition sites. These enzymes are available from New England BioLabs: AscI, PacI; Boehringer Manheim: SwaI and Takara (Japan): Sse8387.

C. Reductase Constructs for Plant Transformation

Constructs for expression of reductase in plant cells using 5' and 3' regulatory regions from a napin gene, are prepared as follows.

A reductase cDNA (in the pCGN1703 vector described above) designated pCGN7571, is digested with SphI (site in 3' untranslated sequence at bases 1594–1599) and a SalI linker is inserted at this site. The resulting plasmid is digested with BamHI and SalI and the fragment containing the reductase cDNA gel purified and cloned into BglII/XhoI digested pCGN3223, the napin cassette described above, resulting in pCGN7585.

A HindIII fragment of pCGN7585 containing the napin 5'/reductase/napin 3' construct is cloned into HindIII digested pCGN1578 (McBride and Summerfelt, supra), resulting in pCGN7586, a binary vector for plant transformation.

Plant transformation construct pCGN7589, also containing the jojoba reductase gene under expression of a napin promoter, is prepared as follows.

pCGN7571 is in vitro mutagenized to introduce an NdeI site at the first ATG of the reductase coding sequence and a BglII site immediately upstream of the NdeI site. BamHI linkers are introduced into the SphI site downstream of the reductase coding region. The 1.5 kb BglII-BamHI fragment is gel purified and cloned into BglII-BamHI digested pCGN3686 (see below), resulting in pCGN7582.

pCGN3686 is a cloning vector derived from Bluescript KS+ (Stratagene Cloning Systems; San Diego, Calif.), but having a chloramphenicol resistance gene and a modified linker region. The source of the chloramphenicol resistance gene, pCGN565 is a cloning vector based on pUC12-cm (K. Buckley Ph.D. Thesis, Regulation and expression of the phi X174 lysis gene, University of California, San Diego, 1985), but containing pUC18 linkers (Yanisch-Perron, et al., *Gene* (1985) 53:103–119). pCGN565 is digested with HhaI and the fragment containing the chloramphenicol resistance gene is excised, blunted by use of mung bean nuclease, and inserted into the EcoRV site of Bluescript KS– (Stratagene: La Jolla, Calif.) to create pCGN2008. The chloramphenicol resistance gene of pCGN2008 is removed by EcoRI/HindIII digestion. After treatment with Klenow enzyme to blunt the ends, the fragment is ligated to DraI digested Bluescript KS+. A clone that has the DraI fragment containing ampicillin resistance replaced with the chloramphenicol resistance is chosen and named pCGN2015. The linker region of pCGN2015 is modified to provide pCGN3686, which contains the following restriction digestion sites, 5' to 3' in the lacZ linker region: PstI, BglII, XhoI, HincII, SalI, HindIII, EcoRV, EcoRI, PstI, SmaI, BamHI, SpeI, XbaI and SacI.

An XhoI linker is inserted at the XbaI site of pCGN7582. The BglII-XhoI fragment containing the reductase gene is isolated and cloned into BglII-XhoI digested pCGN3223. The resulting plasmid, which lacks the 5' untranslated leader sequence from the jojoba gene, is designated pCGN7802. The napin/reductase fragment from pCGN7802 is excised with HindIII and cloned into HindIII digested pCGN1578 to yield pCGN7589.

An additional napin/reductase construct is prepared as follows. The reductase cDNA pCGN7571 (FIG. 1) is mutagenized to insert SalI sites 5' to the ATG start codon (site is 8 base pairs 5' to ATG) and immediately 3' to the TAA translation stop codon, resulting in pCGN7631. pCGN7631 is digested with SalI and the approximately 1.5 kb fragment containing the reductase encoding sequence is cloned into SalI/XhoI digested napin cassette pCGN3223. A resulting plasmid containing the reductase sequence in the sense orientation is designated pCGN7640. pCGN7640 is digested with HindIII, and the fragment containing the oleosin/reductase construct is cloned into HindIII digested binary vector pCGN1559PASS, resulting in binary construct pCGN7642.

A construct for expression of reductase under control of oleosin regulatory regions is prepared as follows. The reductase encoding sequence is obtained by digestion of pCGN7631 with SalI, and ligated into SalI digested pCGN7636, the oleosin cassette. A resulting plasmid containing the reductase sequence in the sense orientation is designated pCGN7641. pCGN7641 is digested with XbaI, and the fragment containing the oleosin/reductase construct is cloned into XbaI digested binary vector pCGN1559PASS, resulting in binary construct pCGN7643.

Binary vector constructs are transformed into Agrobacterium cells, such as of strain EHA101 (Hood et al., *J. Bacteriol* (1986) 168:1291–1301), by the method of Holsters et al. (*Mol. Gen. Genet.* (1978) 163:181–187) and used in plant transformation methods as described below.

Example 7

Assay for Wax Synthesizing Activity

Methods to assay for wax synthase or wax synthesizing capability are described.

A. Radiolabeled Material

The substrate generally used in the wax synthase assays, [1-$^{14}$C]palmitoyl-CoA, is purchased from Amersham (Arlington Heights, Ill.). Other chain length substrates were synthesized in order to perform chain length specification studies. Long chain [1-$^{14}$C] fatty acids (specific activity 51–56 Ci/mole), namely 11-cis-eicosenoic acid, 13-cis-docosenoic acid and 15-cis-tetracosenoic acid are prepared by the reaction of potassium [$^{14}$C]cyanide with the corresponding alcohol mesylate, followed by the base hydrolysis of the alcohol nitrile to the free fatty acid. The free fatty acids are converted to their methyl esters with ethereal diazomethane, and purified by preparative silver nitrate thin layer chromatography (TLC). The fatty acid methyl esters are hydrolyzed back to the free fatty acids. Radiochemical purity is assessed by three TLC methods: normal phase silica TLC, silver nitrate TLC, and C18 reversed phase TLC. Radiochemical purity as measured by these methods was 92–98%. Long chain [1-$^{14}$C] acyl-CoAs are prepared from the corresponding [1-$^{14}$C] free fatty acids by the method of Young and Lynen (*J. Bio. Chem.* (1969) 244:377), to a specific activity of 10 Ci/mole. [1-$^{14}$C]hexadecanal is prepared by the dichromate oxidation of [1-$^{14}$C]hexadecan-1-ol, according to a micro-scale modification of the method of Pletcher and Tate (*Tet. Lett.* (1978) 1601–1602). The product is purified by preparative silica TLC, and stored as a hexane solution at –70° C. until use.

B. Assay for Wax Synthase Activity

Wax synthase activity is measured by incubation of 40 μM [1-$^{14}$C]acyl-CoA (usually palmitoyl-CoA, sp. act. 5.1–5.6 mCi/mmol) and 200 μM oleyl alcohol with the sample to be assayed in a total volume of 0.25 ml. The incubation mixture also contains 20% w/v glycerol, 1 mM DTT, 0.5M NaCl and is buffered with 25 mM HEPES (4-[2-hydroxyethyl]-1-piperazineethane-sulfonic acid). HEPES, here and as referred to hereafter is added from a 1M stock solution adjusted to pH 7.5.

A substrate mixture is prepared in a glass vial, with oleyl alcohol being added immediately before use, and is added to samples. Incubation is carried out at 30° C. for one hour. The assay is terminated by placing the assay tube on ice and immediately adding 0.25 ml isopropanol:acetic acid (4:1 v/v). Unlabeled wax esters (0.1 mg) and oleyl alcohol (0.1 mg) are added as carriers. The [$^{14}$C] lipids are extracted by the scaled-down protocol of Hara and Radin (*Anal. Biochem.* (1978) 90:420). Four ml of hexane/isopropanol (3:2, v/v) is added to the terminated assay. The sample is vortexed, 2 ml of aqueous sodium sulphate solution (6.6% w/v) is added, and the sample is again vortexed.

C. Analysis of Assay Products

The products of the wax synthase assay or the are analyzed as follows.

Following addition of the sodium sulfate and vortexing the sample, a known percentage of the organic phase is removed and counted via liquid scintillation counting. This calculation is used to estimate the total counts in the organic phase. Another portion of the organic phase is then removed, dryed down under nitrogen, redissolved in hexane.

For lipid class analysis the sample is applied to a silica TLC plate, and the plate is developed in hexane/diethyl ether/acetic acid (80:20:1 v/v/v). The distribution of radioactivity between the lipid classes, largely wax esters, free fatty acids, fatty alcohols, and polar lipids at the origin, is measured using an AMBIS radioanalytic imaging system (AMBIS Systems Inc., San Diego, Calif.). If necessary the individual lipid classes can be recovered from the TLC plate for further analysis.

D. Substrate Specificity

Acyl-CoA and alcohol substrates having varying carbon chain lengths and degrees of unsaturation were added to a microsomal membrane fraction having wax synthase activity to determine the range of substrates recognized by the jojoba wax synthase. Wax synthase activity was measured as described in Example 1, with acyl specificity measured using 80 µM of acyl-CoA substrate and 100 µM of radiolabeled oleyl alcohol. Alcohol specificity was measured using 100 µM of alcohol substrate and 40 µM of radiolabeled eicosenoyl-CoA. Results of these experiments are presented in Table 1 below.

TABLE 1

Acyl and Alcohol Substrate Specificity of Jojoba Wax Synthase

| Substrate Structure | Wax synthase Activity (pmoles/min) | |
|---|---|---|
| | Acyl Group | Alcohol Group |
| 12:0 | 12 | 100 |
| 14:0 | 95 | 145 |
| 16:0 | 81 | 107 |
| 18:0 | 51 | 56 |
| 20:0 | 49 | 21 |
| 22:0 | 46 | 17 |
| 18:1 | 22 | 110 |
| 18:2 | 7 | 123 |
| 20:1 | 122 | 72 |
| 22:1 | 39 | 41 |
| 24:1 | 35 | 24 |

The above results demonstrate that the jojoba wax synthase utilizes a broad range of fatty acyl-CoA and fatty alcohol substrates.

In addition, wax synthase activity towards various acyl-thioester substrates was similarly tested using palmitoyl-CoA, palmitoyl-ACP and N-acetyl-S-palmitoyl cysteamine as acyl substrates. The greatest activity was observed with the acyl-CoA substrate. Significant activity (~10% of that with acyl-CoA) was observed with acyl-ACP, but no activity was detectable with the N-acetyl-S-palmitoyl cysteamine substrate.

Example 8

Plant Transformation Methods

A variety of methods have been developed to insert a DNA sequence of interest into the genome of a plant host to obtain the transcription or transcription and translation of the sequence to effect phenotypic changes.

Brassica Transformation

Seeds of high erucic acid, such as cultivar Reston, or Canola-type varieties of *Brassica napus* are soaked in 95% ethanol for 2 min. surface sterilized in a 1.0% solution of sodium hypochlorite containing a drop of Tween 20 for 45 min., and rinsed three times in sterile, distilled water. Seeds are then plated in Magenta boxes with 1/10th concentration of Murashige minimal organics medium (Gibco; Grand Island, N.Y.) supplemented with pyriodoxine (50 µg/l), nicotinic acid (50 µg/l), glycine (200 µg/l), and 0.6% Phytagar (Gibco) pH 5.8. Seeds are germinated in a Percival chamber at 22° C. in a 16 h photoperiod with cool fluorescent and red light of intensity approximately 65µ Einsteins per square meter per second ($\mu Em^{-2}S^{-1}$).

Hypocotyls are excised from 5–7 day old seedlings, cut into pieces approximately 4 mm in length, and plated on feeder plates (Horsch et al., *Science* (1985) 227:1229–1231). Feeder plates are prepared one day before use by plating 1.0 ml of a tobacco suspension culture onto a petri plate (100×25 mm) containing about 30 ml MS salt base (Carolina Biological, Burlington, N.C.) 100 mg/l inositol, 1.3 mg/l thiamine-HCl, 200 mg $KH_2PO_4$ with 3% sucrose, 2,4-D (1.0 mg/l), 0.6% w/v Phytagar, and pH adjusted to 5.8 prior to autoclaving (MS 0/1/0 medium). A sterile filter paper disc (Whatman 3 mm) is placed on top of the feeder layer prior to use. Tobacco suspension cultures are subcultured weekly by transfer of 10 ml of culture into 100 ml fresh MS medium as described for the feeder plates with 2,4-D (0.2 mg/l), Kinetin (0.1 mg/l). In experiments where feeder cells are not used hypocotyl explants are cut and placed onto a filter paper disc on top of MS0/1/0 medium. All hypocotyl explants are preincubated on feeder plates for 24 h. at 22° C. in continuous light of intensity 30 $\mu Em^{-2}S^{-1}$ to 65 $\mu EM^{-2}S^{-1}$.

Single colonies of *A. tumefaciens* strain EHA101 containing a binary plasmid with the desired gene construct are transferred to 5 ml MG/L broth and grown overnight at 30° C. Hypocotyl explants are immersed in 7–12 ml MG/L broth with bacteria diluted to 1×10⁸ bacteria/ml and after 10–25 min. are placed onto feeder plates. Per liter MG/L broth contains 5 g mannitol, 1 g L-Glutamic acid or 1.15 g sodium glutamate, 0.25 g $kH_2PO_4$, 0.10 g NaCl, 0.10 g $MGSO_4 \cdot 7H_2O$, 1 mg biotin, 5 g tryptone, and 2.5 g yeast extract, and the broth is adjusted to pH 7.0. After 48 hours of co-incubation with Agrobacterium, the hypocotyl explants are transferred to B5 0/1/0 callus induction medium which contains filter sterilized carbenicillin (500 mg/l, added after autoclaving) and kanamycin sulfate (Boehringer Mannheim; Indianapolis, Ind.) at concentrations of 25 mg/l.

After 3–7 days in culture at 65 $\mu EM^{-2}S^{-1}$ continuous light, callus tissue is visible on the cut surface and the hypocotyl explants are transferred to shoot induction medium, B5BZ (B5 salts and vitamins supplemented with 3 mg/l benzylaminopurine, 1 mg/l zeatin, 1% sucrose, 0.6% Phytagar and pH adjusted to 5.8). This medium also contains carbenicillin (500 mg/l) and kanamycin sulfate (25 mg/l). Hypocotyl explants are subcultured onto fresh shoot induction medium every two weeks.

Shoots regenerate from the hypocotyl calli after one to three months. Green shoots at least 1 cm tall are excised from the calli and placed on medium containing B5 salts and vitamins, 1% sucrose, carbenicillin (300 mg/l), kanamycin sulfate (50 mg/l) and 0.6% w/v Phytagar). After 2–4 weeks shoots which remain green are cut at the base and transferred to Magenta boxes containing root induction medium (B5 salts and vitamins, 1% sucrose, 2 mg/l indolebutyric acid, 50 mg/l kanamycin sulfate and 0.6% Phytagar). Green rooted shoots are tested for thioesterase activity.

Arabidposis Transformation

Transgenic *Arabidopsis thaliana* plants may be obtained by Agrobacterium-mediated transformation as described by Valverkens et al., (*Proc. Nat. Acad. Sci.* (1988) 85:5536–5540). Constructs are transformed into Agrobacterium cells, such as of strain EHA101 (Hood et al., *J. Bacteriol* (1986) 168:1291–1301), by the method of Holsters et al. (*Mol. Gen. Genet.* (1978) 163:181–187).

Peanut Transformation

DNA sequences of interest may be introduced as expression cassettes, comprising at least a promoter region, a gene of interest, and a termination region, into a plant genome via particle bombardment.

Briefly, tungsten or gold particles of a size ranging from 0.5 mM–3 mM are coated with DNA of an expression cassette. This DNA may be in the form of an aqueous mixture or a dry DNA/particle precipitate.

Tissue used as the target for bombardment may be from cotyledonary explants, shoot meristems, immature leaflets, or anthers. The bombardment of the tissue with the DNA-coated particles is carried out using a Biolistics™ particle gun (Dupont; Wilmington, Del.). The particles are placed in the barrel at variable distances ranging from 1 cm–14 cm from the barrel mouth. The tissue to be bombarded is placed beneath the stopping plate; testing is performed on the tissue at distances up to 20 cm. At the moment of discharge, the tissue is protected by a nylon net or a combination of nylon nets with mesh ranging from 10 mM to 300 mM.

Following bombardment, plants may be regenerated following the method of Atreya, et al., (*Plant Science Letters* (1984) 34:379–383). Briefly, embryo axis tissue or cotyledon segments are placed on MS medium (Murashige and Skoog, *Physio. Plant.* (1962) 15:473) (MS plus 2.0 mg/l 6-benzyladenine (BA) for the cotyledon segments) and incubated in the dark for 1 week at 25±2° C. and are subsequently transferred to continuous cool white fluorescent light (6.8 W/m$^2$). On the 10th day of culture, the plantlets are transferred to pots containing sterile soil, are kept in the shade for 3–5 days are and finally moved to greenhouse. The putative transgenic shoots are rooted. Integration of exogenous DNA into the plant genome may be confirmed by various methods know to those skilled in the art.

Developing seeds from Arabidopsis plants transformed with the pCGN7586 napin/reductase construct, are analyzed for reductase activity as described in Example 1C. Out of fifteen plants analyzed, eleven were found to have reductase enzyme activity, with specific activities ranging from 5 to 30 pmol/min/mg protein. Western analysis demonstrates that the amount of reductase present in transgenic Arabidopsis embryos is approximately 0.01% of total protein.

Example 9

Analysis of Transformed Plants

Transformed plants are assayed to measure fatty alcohol and wax ester components as described herein. Such plants may be prepared by Agrobacterium transformation methods as described above. Plants may be assayed for the presence of wax esters, for example by separation of triacylglycerides (TAG) from wax esters by TLC. GC analysis methods may be used to further analyze the resulting waxes.

A. Gas Chromatography (GC) Analysis of Transformed Plants

The content of unesterified or crude oil will not pass through a typical GC column due to the high temperatures necessary to burn off the TAG component (approximately 350° C. to 365° C.). The SUPELCOWAX™ 10 column, for instance, has a top temperature range of approximately 280° C.

Lipids are extracted from mature seeds of Arabidopsis, derivatized (Browse et al. (1986) *Anal. Biochem.* 152:141–145) and analyzed for alcohol content by GC as described above. These analyses reveal the presence of 20:1 alcohol in 3 of the transformed Arabidopsis plants.

The oil of seeds from control rapeseed plants and pCGN7643 rapeseed plants is similarly transesterified, in methanol/H$_2$SO$_4$, by the following method. Twenty-five (25) seeds from each plant are incubated in 4 ml H$_2$SO$_4$ in methanol (5%) at 80° C. for 90 minutes. To this incubated mixture 1 ml of 0.9% NaCl, and 1 ml of hexane are added, and the upper organic phase is removed for analysis. Gas chromatography (GC) analysis on a SUPELCOWAX™ 10 column shows that the pCGN7643 samples contain 22:1 alcohol while the untransformed control plants do not contain the alcohol. The identity of this peak as an alcohol is confirmed using a Mass Spectrometer (MS).

Crude oil from the T2 seeds is also analyzed. Twenty-five (25) seeds from each plant are pooled and homogenized in 2 ml of hexane. The extract is filtered and high temperature GC analysis is performed using a CHROMPAK™ triglyceride column (maximum temperature of approximately 370° C.). This column is suitable for analysis of TAG as well as waxes Several peaks with retention times consistent with wax esters are detected in the pCGN7643 samples, however there are no peaks observed which are consistent with a fatty alcohol. The wax ester peaks are not present in the untransformed control samples. The most prominent peak has a retention time consistent with its being a 40:2 wax ester. As the only detected fatty alcohol in the transesterified oil is 22:1 alcohol, this prominent wax ester is believed to comprise an 18:1 fatty acid esterified to a 22:1 fatty alcohol.

A high temperature GC analysis protocol is used to further analyze the transformed rapeseed oil which has been transesterified in methanol/H$_2$SO$_4$. Wax ester peaks are not present in the transesterified oil from pCGN7643 plants. This is expected since transesterification produces fatty acid methyl esters and alcohols from the wax component of the oil. The 22:1 fatty alcohol component of the derivatized oil is present in seed of some of the transformed rape plants as component which is estimated to comprise about 0.5% of total lipids, as measured by weight. Since the fatty alcohol substrate of the wax ester contributes approximately one-half of the total weight of the wax ester, it is seen that wax ester can be produced as a component of about 1.0% by weight in transformed oil.

High temperature GC/MS analysis is performed on the T2 seed oil of rapeseed plants using the CHROMPAK™ triglyceride column. Mass chromatograms (selected ion monitoring) of the T2 oil showed peaks with retention times and masses consistent with the presence of 38:2, 40:2, 42:2 and 44:2 wax esters in the transgenic oil. These peaks are not detected in the control oil. The mass spectrum of the 40:2 wax ester peak verified that it is comprised of a 22:1 alcohol and an 18:1 fatty acid.

High temperature GC analysis of the oil from T3 seeds of a pCGN7643 plant using the triglyceride column shows that the transgenic oil contains the 40:2 wax ester peak characterized by GC/MS analysis in the T2 seed oil. The wax ester peak is not detected in the untransformed control oil.

B. Analysis of Purified Wax Fractions

Preparative thin layer chromatography is used to enrich the rapeseed oil samples in waxes, and eliminate triglycerides from the oil. The oil samples are spotted onto Silica-G TLC plates and developed in Hexane:ethyl acetate (95:5). The location of wax bands are identified by iodine staining. The wax fraction is eluted from the silica medium with Hexane:ethyl acetate (70:30), dried under nitrogen gas, and resuspended in hexane. The wax fractions are then analyzed by high temperature GC using the triglyceride column. The 40:2 wax ester peak is one of the most abundant species present in the samples from pCGN7643 plants, but is not present in untransformed control samples.

The TLC purified wax is then transesterified with methanol/$H_2SO_4$. High temperature GC analysis shows that the wax peaks are no longer present in the samples. This is expected since the transesterification should produce fatty acid methyl esters and alcohols from wax esters.

GC analysis of the transesterified wax fractions using the SUPELCOWAX™10 column shows that the transgenic samples contain a prominent 22:1 fatty alcohol peak. The fraction from the control samples does not contain the fatty alcohol.

The above results demonstrate the ability to produce wax ester in a plant cell by a method comprising the step of growing a plant cell having a fatty acyl reductase expressed from a sequence heterologous to the plant. Cells containing long chain wax ester which have been transformed by jojoba reductase nucleic acid sequences are exemplified. Methods are provided whereby other reductase proteins and encoding sequences may be obtained to produce alternative fatty alcohols and waxes in plant cells.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity and understanding, it will be readily apparent to those of ordinary skill in the art in light of the teaching of this invention that certain changes and modifications may be made thereto without departing from the spirit or scope of the appended claims.

What is claimed is:

1. A method of producing a wax ester in a plant cell, wherein said method comprises growing a plant cell comprising a jojoba fatty acyl reductase expressed from a sequence heterologous to said plant cell, wherein said plant cell comprises a fatty acyl substrate of said jojoba fatty acyl reductase.

2. The method of claim 1 wherein said reductase is expressed from a recombinant construct which comprises a nucleic acid sequence encoding said reductase under the control of regulatory elements functional in a plant seed cell.

3. The method of claim 1 wherein said reductase encoding sequence is as shown in FIG. 1 (SEQ ID NO:19).

4. The method of claim 1 wherein said plant cell is a seed embryo cell.

5. The method of claim 1 wherein said plant cell is a cruciferous plant cell.

6. The method of claim 5 wherein said cell is a Brassica cell.

7. The method of claim 5 wherein said cell is an Arabidopsis cell.

8. A plant cell comprising a wax ester obtained by the method of claim 1.

9. A rapeseed plant seed cell according to claim 8 wherein crude oil of seed seed cell comprises greater than about 0.5% wax ester by weight.

10. A cell according to claim 9 wherein said crude oil comprises greater than about 1.0% wax ester by weight.

11. A plant comprising a plant cell according to claim 8.

* * * * *

SEQUENCE LISTING ( 1 ) GENERAL INFORMATION:

( i i i ) NUMBER OF SEQUENCES: 19

( 2 ) INFORMATION FOR SEQ ID NO: 1:

( i ) SEQUENCE CHARACTERISTICS:
( A ) LENGTH: 13 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Ala Ile Leu Val Thr Gly Ala Thr Gly Ser Leu Ala Lys
            5                       10

( 2 ) INFORMATION FOR SEQ ID NO: 2:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( x i ) SEQUENCE DESCRIPTION: SEQ ID NO:2:

Leu Gln Asn Glu Xaa Phe Gly Lys Glu Leu Phe Lys
            5                       10

( 2 ) INFORMATION FOR SEQ ID NO: 3:

( i ) SEQUENCE CHARACTERISTICS:
( A ) LENGTH: 13 amino acids
( B ) TYPE: amino acid
( D ) TOPOLOGY: linear ( i i ) MOLECULE TYPE: peptide ( x i ) SEQUENCE DESCRIPTION: SEQ ID NO:3:

Val Thr Val Val Pro Gly Asp Ile Thr Gly Glu Asp Leu
            5                       10

( 2 ) INFORMATION FOR SEQ ID NO: 4:

( i ) SEQUENCE CHARACTERISTICS:
( A ) LENGTH: 9 amino acids
( B ) TYPE: amino acid
( D ) TOPOLOGY: linear ( i i ) MOLECULE TYPE: peptide ( x i ) SEQUENCE DESCRIPTION: SEQ ID NO:4:

Leu Gly Leu Asp Ile Asn Val Glu Lys
            5

( 2 ) INFORMATION FOR SEQ ID NO: 5:

( i ) SEQUENCE CHARACTERISTICS:
      ( A ) LENGTH: 11 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:5:

Thr Ile Asp Asn Val Pro Val Tyr Tyr Gly Lys
            5                          10

( 2 ) INFORMATION FOR SEQ ID NO: 6:

( i ) SEQUENCE CHARACTERISTICS:
      ( A ) LENGTH: 17 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:6:

Tyr Val Glu Pro Val Thr Tyr His Val Gly Ser Ser Ala Ala Asn Pro Met
            5                          10                        15

( 2 ) INFORMATION FOR SEQ ID NO: 7:

( i ) SEQUENCE CHARACTERISTICS:
      ( A ) LENGTH: 10 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:7:

Leu Ser Ala Leu Pro Glu Met Ala His Arg
            5                          10

( 2 ) INFORMATION FOR SEQ ID NO: 8:

( i ) SEQUENCE CHARACTERISTICS:
      ( A ) LENGTH: 6 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:8:

Leu Val Asp Ile Tyr Lys
            5

( 2 ) INFORMATION FOR SEQ ID NO: 9:

( i ) SEQUENCE CHARACTERISTICS:
      ( A ) LENGTH: 12 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:9:

Glu Gly Ile Val Glu Ala Asp Met Phe Tyr Phe Asp ( 2 ) INFORMATION FOR SEQ ID NO: 10:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Ala Ile Asn Trp Glu Asp Tyr Phe Leu Lys Thr Xaa Phe Pro Gly Val Val
              5                      10                15

Glu Xaa Val Leu
      20

( 2 ) INFORMATION FOR SEQ ID NO: 11:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Ala Ile Leu Val Thr Gly Ala Thr Gly Ser Leu Ala Lys
            5                    10

( 2 ) INFORMATION FOR SEQ ID NO: 12:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Leu Gly Leu Asp Ile Asn Val Glu Lys
            5

( 2 ) INFORMATION FOR SEQ ID NO: 13:

( i ) SEQUENCE CHARACTERISTICS:
        ( A ) LENGTH: 10 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Thr Ile Asp Asn Val Pro Val Tyr Tyr Gly
            5                   10

( 2 ) INFORMATION FOR SEQ ID NO: 14:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

Tyr Val Glu Pro Val Thr Tyr Xaa Val Gly Ser Ser Ala Ala Asn
            5                    10              15

( 2 ) INFORMATION FOR SEQ ID NO: 15:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Leu Val Asp Ile Tyr Lys Pro
              5

( 2 ) INFORMATION FOR SEQ ID NO: 16:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Glu Gly Ile Val Glu Ala Asp Met Phe Tyr Phe
              5                      10

( 2 ) INFORMATION FOR SEQ ID NO: 17:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

Ala Ile Asn Trp Glu Asp Tyr Phe Leu
              5

( 2 ) INFORMATION FOR SEQ ID NO: 18:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

Thr His Phe Pro Gly Val Val Glu His Val Leu
              5                      10

( 2 ) INFORMATION FOR SEQ ID NO: 19:

( i ) SEQUENCE CHARACTERISTICS:
        ( A ) LENGTH: 1786 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:19:

```
AAATCCTCCA CTCATACACT CCACTTCTCT CTCTCTCTCT CTCTCTCTGA AACAATTTGA          60

GTAGCAAACT TAAAAGAAA ATG GAG GAA ATG GGA AGC ATT TTA GAG TTT CTT         112
                    Met Glu Glu Met Gly Ser Ile Leu Glu Phe Leu
                     1               5                      10

GAT AAC AAA GCC ATT TTG GTC ACT GGT GCT ACT GGC TCC TTA GCA AAA          160
```

|   |   |   |   |   |   |   |   |   |   |   |   |   |   |   |   |      |
|---|---|---|---|---|---|---|---|---|---|---|---|---|---|---|---|------|
| Asp | Asn | Lys | Ala | Ile | Leu | Val | Thr | Gly | Ala | Thr | Gly | Ser | Leu | Ala | Lys | |
|   |   | 15 |   |   |   | 20 |   |   |   |   | 25 |   |   |   |   |      |

| ATT | TTT | GTG | GAG | AAG | GTA | CTG | AGG | AGT | CAA | CCG | AAT | GTG | AAG | AAA | CTC | 208 |
|---|---|---|---|---|---|---|---|---|---|---|---|---|---|---|---|---|
| Ile | Phe | Val | Glu | Lys | Val | Leu | Arg | Ser | Gln | Pro | Asn | Val | Lys | Lys | Leu |  |
|  | 30 |  |  |  |  | 35 |  |  |  |  | 40 |  |  |  |  |  |

| TAT | CTT | CTT | TTG | AGA | GCA | ACC | GAT | GAC | GAG | ACA | GCT | GCT | CTA | CGC | TTG | 256 |
|---|---|---|---|---|---|---|---|---|---|---|---|---|---|---|---|---|
| Tyr | Leu | Leu | Leu | Arg | Ala | Thr | Asp | Asp | Glu | Thr | Ala | Ala | Leu | Arg | Leu |  |
| 45 |  |  |  |  | 50 |  |  |  |  | 55 |  |  |  |  | 60 |  |

| CAA | AAT | GAG | GTT | TTT | GGA | AAA | GAG | TTG | TTC | AAA | GTT | CTG | AAA | CAA | AAT | 304 |
|---|---|---|---|---|---|---|---|---|---|---|---|---|---|---|---|---|
| Gln | Asn | Glu | Val | Phe | Gly | Lys | Glu | Leu | Phe | Lys | Val | Leu | Lys | Gln | Asn |  |
|  |  |  |  |  | 65 |  |  |  | 70 |  |  |  |  | 75 |  |  |

| TTA | GGT | GCA | AAT | TTC | TAT | TCC | TTT | GTA | TCA | GAA | AAA | GTG | ACT | GTA | GTA | 352 |
|---|---|---|---|---|---|---|---|---|---|---|---|---|---|---|---|---|
| Leu | Gly | Ala | Asn | Phe | Tyr | Ser | Phe | Val | Ser | Glu | Lys | Val | Thr | Val | Val |  |
|  |  |  | 80 |  |  |  |  | 85 |  |  |  |  | 90 |  |  |  |

| CCC | GGT | GAT | ATT | ACT | GGT | GAA | GAC | TTG | TGT | CTC | AAA | GAC | GTC | AAT | TTG | 400 |
|---|---|---|---|---|---|---|---|---|---|---|---|---|---|---|---|---|
| Pro | Gly | Asp | Ile | Thr | Gly | Glu | Asp | Leu | Cys | Leu | Lys | Asp | Val | Asn | Leu |  |
|  |  | 95 |  |  |  |  | 100 |  |  |  |  | 105 |  |  |  |  |

| AAG | GAA | GAA | ATG | TGG | AGG | GAA | ATC | GAT | GTT | GTT | GTC | AAT | CTA | GCT | GCT | 448 |
|---|---|---|---|---|---|---|---|---|---|---|---|---|---|---|---|---|
| Lys | Glu | Glu | Met | Trp | Arg | Glu | Ile | Asp | Val | Val | Val | Asn | Leu | Ala | Ala |  |
|  |  | 110 |  |  |  |  | 115 |  |  |  |  | 120 |  |  |  |  |

| ACA | ATC | AAC | TTC | ATT | GAA | AGG | TAC | GAC | GTG | TCT | CTG | CTT | ATC | AAC | ACA | 496 |
|---|---|---|---|---|---|---|---|---|---|---|---|---|---|---|---|---|
| Thr | Ile | Asn | Phe | Ile | Glu | Arg | Tyr | Asp | Val | Ser | Leu | Leu | Ile | Asn | Thr |  |
| 125 |  |  |  |  | 130 |  |  |  |  | 135 |  |  |  |  | 140 |  |

| TAT | GGA | GCC | AAG | TAT | GTT | TTG | GAC | TTC | GCG | AAG | AAG | TGC | AAC | AAA | TTA | 544 |
|---|---|---|---|---|---|---|---|---|---|---|---|---|---|---|---|---|
| Tyr | Gly | Ala | Lys | Tyr | Val | Leu | Asp | Phe | Ala | Lys | Lys | Cys | Asn | Lys | Leu |  |
|  |  |  |  | 145 |  |  |  |  | 150 |  |  |  |  | 155 |  |  |

| AAG | ATA | TTT | GTT | CAT | GTA | TCT | ACT | GCT | TAT | GTA | TCT | GGA | GAG | AAA | AAT | 592 |
|---|---|---|---|---|---|---|---|---|---|---|---|---|---|---|---|---|
| Lys | Ile | Phe | Val | His | Val | Ser | Thr | Ala | Tyr | Val | Ser | Gly | Glu | Lys | Asn |  |
|  |  |  |  | 160 |  |  |  |  | 165 |  |  |  |  | 170 |  |  |

| GGG | TTA | ATA | CTG | GAG | AAG | CCT | TAT | TAT | ATG | GGC | GAG | TCA | CTT | AAT | GGA | 640 |
|---|---|---|---|---|---|---|---|---|---|---|---|---|---|---|---|---|
| Gly | Leu | Ile | Leu | Glu | Lys | Pro | Tyr | Tyr | Met | Gly | Glu | Ser | Leu | Asn | Gly |  |
|  |  | 175 |  |  |  |  | 180 |  |  |  |  | 185 |  |  |  |  |

| AGA | TTA | GGT | CTG | GAC | ATT | AAT | GTA | GAG | AAG | AAA | CTT | GTG | GAG | GCA | AAA | 688 |
|---|---|---|---|---|---|---|---|---|---|---|---|---|---|---|---|---|
| Arg | Leu | Gly | Leu | Asp | Ile | Asn | Val | Glu | Lys | Lys | Leu | Val | Glu | Ala | Lys |  |
|  | 190 |  |  |  |  | 195 |  |  |  |  | 200 |  |  |  |  |  |

| ATC | AAT | GAA | CTT | CAA | GCA | GCG | GGG | GCA | ACG | GAA | AAG | TCC | ATT | AAA | TCG | 736 |
|---|---|---|---|---|---|---|---|---|---|---|---|---|---|---|---|---|
| Ile | Asn | Glu | Leu | Gln | Ala | Ala | Gly | Ala | Thr | Glu | Lys | Ser | Ile | Lys | Ser |  |
| 205 |  |  |  |  | 210 |  |  |  |  | 215 |  |  |  |  | 220 |  |

| ACA | ATG | AAG | GAC | ATG | GGC | ATC | GAG | AGG | GCA | AGA | CAC | TGG | GGA | TGG | CCA | 784 |
|---|---|---|---|---|---|---|---|---|---|---|---|---|---|---|---|---|
| Thr | Met | Lys | Asp | Met | Gly | Ile | Glu | Arg | Ala | Arg | His | Trp | Gly | Trp | Pro |  |
|  |  |  |  | 225 |  |  |  |  | 230 |  |  |  |  | 235 |  |  |

| AAT | GTG | TAT | GTA | TTC | ACC | AAG | GCA | TTA | GGG | GAG | ATG | CTT | TTG | ATG | CAA | 832 |
|---|---|---|---|---|---|---|---|---|---|---|---|---|---|---|---|---|
| Asn | Val | Tyr | Val | Phe | Thr | Lys | Ala | Leu | Gly | Glu | Met | Leu | Leu | Met | Gln |  |
|  |  |  | 240 |  |  |  |  | 245 |  |  |  |  | 250 |  |  |  |

| TAC | AAA | GGG | GAC | ATT | CCG | CTT | ACT | ATT | ATT | CGT | CCC | ACC | ATC | ATC | ACC | 880 |
|---|---|---|---|---|---|---|---|---|---|---|---|---|---|---|---|---|
| Tyr | Lys | Gly | Asp | Ile | Pro | Leu | Thr | Ile | Ile | Arg | Pro | Thr | Ile | Ile | Thr |  |
|  |  | 255 |  |  |  |  | 260 |  |  |  |  | 265 |  |  |  |  |

| AGC | ACT | TTT | AAA | GAG | CCC | TTT | CCT | GGT | TGG | GTT | GAA | GGT | GTC | AGG | ACC | 928 |
|---|---|---|---|---|---|---|---|---|---|---|---|---|---|---|---|---|
| Ser | Thr | Phe | Lys | Glu | Pro | Phe | Pro | Gly | Trp | Val | Glu | Gly | Val | Arg | Thr |  |
|  | 270 |  |  |  |  | 275 |  |  |  |  | 280 |  |  |  |  |  |

| ATC | GAT | AAT | GTA | CCT | GTA | TAT | TAT | GGT | AAA | GGG | AGA | TTG | AGG | TGT | ATG | 976 |
|---|---|---|---|---|---|---|---|---|---|---|---|---|---|---|---|---|
| Ile | Asp | Asn | Val | Pro | Val | Tyr | Tyr | Gly | Lys | Gly | Arg | Leu | Arg | Cys | Met |  |
| 285 |  |  |  |  | 290 |  |  |  |  | 295 |  |  |  |  | 300 |  |

| CTT | TGC | GGA | CCC | AGC | ACA | ATA | ATT | GAC | CTG | ATA | CCG | GCA | GAT | ATG | GTC | 1024 |
|---|---|---|---|---|---|---|---|---|---|---|---|---|---|---|---|---|
| Leu | Cys | Gly | Pro | Ser | Thr | Ile | Ile | Asp | Leu | Ile | Pro | Ala | Asp | Met | Val |  |
|  |  |  |  | 305 |  |  |  |  | 310 |  |  |  |  | 315 |  |  |

| GTG | AAT | GCA | ACG | ATA | GTA | GCC | ATG | GTG | GCG | CAC | GCA | AAC | CAA | AGA | TAC | 1072 |
|---|---|---|---|---|---|---|---|---|---|---|---|---|---|---|---|---|
| Val | Asn | Ala | Thr | Ile | Val | Ala | Met | Val | Ala | His | Ala | Asn | Gln | Arg | Tyr |  |
|  |  |  | 320 |  |  |  |  | 325 |  |  |  |  | 330 |  |  |  |

| GTA | GAG | CCG | GTG | ACA | TAC | CAT | GTG | GGA | TCT | TCA | GCG | GCG | AAT | CCA | ATG | 1120 |

| | | | | | | | | | | | | | | | |
|---|---|---|---|---|---|---|---|---|---|---|---|---|---|---|---|
| Val | Glu | Pro | Val | Thr | Tyr | His | Val | Gly | Ser | Ser | Ala | Ala | Asn | Pro | Met |
| | | 335 | | | | | 340 | | | | | 345 | | | |

| | | | | | | | | | | | | | | | | |
|---|---|---|---|---|---|---|---|---|---|---|---|---|---|---|---|---|
| AAA | CTG | AGT | GCA | TTA | CCA | GAG | ATG | GCA | CAC | CGT | TAC | TTC | ACC | AAG | AAT | 1168 |
| Lys | Leu | Ser | Ala | Leu | Pro | Glu | Met | Ala | His | Arg | Tyr | Phe | Thr | Lys | Asn | |
| | 350 | | | | | 355 | | | | | 360 | | | | | |
| CCA | TGG | ATC | AAC | CCG | GAT | CGC | AAC | CCA | GTA | CAT | GTG | GGT | CGG | GCT | ATG | 1216 |
| Pro | Trp | Ile | Asn | Pro | Asp | Arg | Asn | Pro | Val | His | Val | Gly | Arg | Ala | Met | |
| 365 | | | | | 370 | | | | | 375 | | | | | 380 | |
| GTC | TTC | TCC | TCC | TTC | TCC | ACC | TTC | CAC | CTT | TAT | CTC | ACC | CTT | AAT | TTC | 1264 |
| Val | Phe | Ser | Ser | Phe | Ser | Thr | Phe | His | Leu | Tyr | Leu | Thr | Leu | Asn | Phe | |
| | | | | 385 | | | | | 390 | | | | | 395 | | |
| CTC | CTT | CCT | TTG | AAG | GTA | CTG | GAG | ATA | GCA | AAT | ACA | ATA | TTC | TGC | CAA | 1312 |
| Leu | Leu | Pro | Leu | Lys | Val | Leu | Glu | Ile | Ala | Asn | Thr | Ile | Phe | Cys | Gln | |
| | | | 400 | | | | | 405 | | | | | 410 | | | |
| TGG | TTC | AAG | GGT | AAG | TAC | ATG | GAT | CTT | AAA | AGG | AAG | ACG | AGG | TTG | TTG | 1360 |
| Trp | Phe | Lys | Gly | Lys | Tyr | Met | Asp | Leu | Lys | Arg | Lys | Thr | Arg | Leu | Leu | |
| | | 415 | | | | | 420 | | | | | 425 | | | | |
| TTG | CGT | TTA | GTA | GAC | ATT | TAT | AAA | CCC | TAC | CTC | TTC | TTC | CAA | GGC | ATC | 1408 |
| Leu | Arg | Leu | Val | Asp | Ile | Tyr | Lys | Pro | Tyr | Leu | Phe | Phe | Gln | Gly | Ile | |
| | 430 | | | | | 435 | | | | | 440 | | | | | |
| TTT | GAT | GAC | ATG | AAC | ACT | GAG | AAG | TTG | CGG | ATT | GCT | GCA | AAA | GAA | AGC | 1456 |
| Phe | Asp | Asp | Met | Asn | Thr | Glu | Lys | Leu | Arg | Ile | Ala | Ala | Lys | Glu | Ser | |
| 445 | | | | | 450 | | | | | 455 | | | | | 460 | |
| ATA | GTT | GAA | GCT | GAT | ATG | TTT | TAC | TTT | GAT | CCC | AGG | GCA | ATT | AAC | TGG | 1504 |
| Ile | Val | Glu | Ala | Asp | Met | Phe | Tyr | Phe | Asp | Pro | Arg | Ala | Ile | Asn | Trp | |
| | | | | 465 | | | | | 470 | | | | | 475 | | |
| GAA | GAT | TAC | TTC | TTG | AAA | ACT | CAT | TTC | CCA | GGN | GTC | GTA | GAG | CAC | GTT | 1552 |
| Glu | Asp | Tyr | Phe | Leu | Lys | Thr | His | Phe | Pro | Gly | Val | Val | Glu | His | Val | |
| | | | 480 | | | | | 485 | | | | | 490 | | | |

| | | | | | |
|---|---|---|---|---|---|
| CTT | AAC | TAAAAGTTAC | GGTACGAAAA | TGAGAAGATT GGAATGCATG | CACCGAAAGN | 1608 |
| Leu | Asn | | | | |

NCAACATAAA AGACGTGGTT AAAGTCATGG TCAAAAAAGA AATAAAATGC AGTTAGGTTT 1668

GTGTTGCAGT TTTGATTCCT TGTATTGTTA CTTGTACTTT TGATCTTTTT CTTTTTAAT 1728

GAAATTTCTC TCTTTGTTTT GTGAAAAAAA AAAAAAAAAA GAGCTCCTGC AGAAGCTT 1786